US009933393B2

(12) United States Patent
Georgeson et al.

(10) Patent No.: US 9,933,393 B2
(45) Date of Patent: Apr. 3, 2018

(54) APPARATUSES, METHODS, AND SYSTEMS FOR INSPECTING A COMPOSITE END PORTION OF A PART

(71) Applicant: The Boeing Company, Chicago, IL (US)

(72) Inventors: Gary Georgeson, Tacoma, WA (US); Barry Fetzer, Renton, WA (US); William Paul Motzer, Seattle, WA (US)

(73) Assignee: The Boeing Company, Chicago, IL (US)

( * ) Notice: Subject to any disclaimer, the term of this patent is extended or adjusted under 35 U.S.C. 154(b) by 281 days.

(21) Appl. No.: 14/964,496

(22) Filed: Dec. 9, 2015

(65) Prior Publication Data

US 2017/0168022 A1 Jun. 15, 2017

(51) Int. Cl.
*G01N 35/00* (2006.01)
*G01N 29/04* (2006.01)

(52) U.S. Cl.
CPC ....... *G01N 29/043* (2013.01); *G01N 35/0099* (2013.01); *G01N 2291/106* (2013.01); *G01N 2291/2694* (2013.01)

(58) Field of Classification Search
CPC ............ G01N 29/043; G01N 35/0099; G01N 2291/106; G01N 2291/2694
USPC ........................................................ 73/628
See application file for complete search history.

(56) References Cited

U.S. PATENT DOCUMENTS

| 4,461,178 | A | 7/1984 | Chamuel |
| 5,698,787 | A | 12/1997 | Parzuchowski et al. |
| 6,378,387 | B1 | 4/2002 | Froom |
| 7,640,811 | B2 | 1/2010 | Kennedy et al. |
| 8,276,452 | B2 | 10/2012 | Takeishi et al. |
| 8,468,890 | B2 | 6/2013 | Shimazaki et al. |
| 8,783,111 | B2 | 7/2014 | Matsumoto et al. |
| 8,978,478 | B2 | 3/2015 | Ishioka |
| 2007/0227250 | A1* | 10/2007 | Kennedy ............... G01N 29/225 73/641 |
| 2010/0263450 | A1* | 10/2010 | Bobrek ..................... B22F 3/15 73/622 |
| 2011/0177603 | A1 | 7/2011 | Ninomiya et al. |
| 2012/0067129 | A1* | 3/2012 | Fujiwara .............. G01N 29/225 73/644 |
| 2012/0250970 | A1* | 10/2012 | Tsubaki ............. G01N 29/0654 382/131 |

(Continued)

Primary Examiner — J M Saint Surin
(74) Attorney, Agent, or Firm — Kolisch Hartwell, P.C.

(57) ABSTRACT

Apparatuses, systems, and methods for inspecting a composite end portion of a part are disclosed. The apparatus may include first and second members having first and second contact elements, respectively. The second member may be movably connected to the first member. The first and second members may be shaped to define a gap sized to receive the end portion. The apparatus may include at least one ultrasonic array supported by at least one of the first and second members. The at least one ultrasonic array may be configured to transmit ultrasonic waves toward the end portion. The apparatus may include a fluid conduit having first and second ends through one of the first and second members. The first end may be configured to be coupled to a suction system, and the second end of the fluid conduit may be configured to be adjacent to a contact surface of the part.

32 Claims, 20 Drawing Sheets

(56) References Cited

U.S. PATENT DOCUMENTS

2013/0276540 A1* 10/2013 Fujiwara .............. G01N 29/043
 73/629
2015/0013463 A1 1/2015 Georgeson et al.
2017/0284973 A1* 10/2017 Falter ................... G01N 29/225

* cited by examiner

APPARATUSES, METHODS, AND SYSTEMS FOR INSPECTING A COMPOSITE END PORTION OF A PART

FIELD

The present invention relates generally to composite end portions of a part, and more specifically to apparatuses, methods, and systems for inspecting the composite end portions of a part.

BACKGROUND

A part may be made of one or more suitable materials. For example, a part may be made of a composite material, which typically are made from two or more constituent materials with significantly different physical or chemical properties. Typically, the constituent materials include a matrix (or bond) material, such as resin (e.g., thermoset epoxy), and a reinforcement material, such as a plurality of fibers (e.g., a woven layer of carbon fibers). When combined, the constituent materials typically produce a composite material with characteristics different from the individual constituent materials even though the constituent materials generally remain separate and distinct within the finished structure of the composite material. Carbon-fiber-reinforced polymer is an example of such a composite material.

Composite materials may be preferred for many reasons. For example, composite materials may be stronger and/or lighter than traditional materials. As a result, composite materials are generally used to construct various objects, such as vehicles (e.g., airplanes, automobiles, boats, bicycles, and/or components thereof), and non-vehicle structures (e.g., buildings, bridges, swimming pool panels, shower stalls, bathtubs, storage tanks, and/or components thereof). Parts that are largely two-dimensional but with a definite thickness, such as the outer skin of an aircraft wing, are often constructed of a plurality of layers of reinforcement material, the layers impregnated with matrix material and bonded to adjacent layers by the matrix material.

Composite structures may have defects, such as delaminations where adjacent layers separate from one another. Other defects may include holes or other unintended voids in the structure which may create an unwanted degree of porosity. Defects such as these can adversely affect the material properties of the part. These defects can be created during a curing process that creates a composite part, when an edge of a part is created by cutting or drilling, when an existing edge is beveled, chamfered, radiused or otherwise trimmed, or as stress is applied to the part over time during use of the part, among others.

Often, a part is inspected for defects after it has been created. In cases where the part is subsequently cut and/or trimmed, the part may then be inspected again. In particular, the part may be inspected near where the cutting and/or trimming took place. Inspecting and then reinspecting a part may be unnecessarily costly and inefficient.

In the case where a composite end portion (such as a trimmed edge of a part) is inspected, two separate apparatuses are often used: a first apparatus to inspect the trimmed edge of the part and a second apparatus to inspect the part proximate the trimmed edge. Using two separate apparatuses may be inefficient and integrating the results of the two inspections may be difficult.

In the case where an edge of a part is inspected, often an apparatus is used to inspect one side of the part proximate the edge and then used again to inspect the other side of the part proximate the edge. Again, having multiple passes of an apparatus over an area may be inefficient.

Finally, composite end portions of parts are often inspected by moving an inspection apparatus around the edge by hand. This method introduces the possibility of human error and inconsistency. On the other hand, if an automated robotic system were used to move the inspection apparatus around, very precise and difficult planning of the route of the apparatus to maintain the appropriate alignment with the composite end portion may be required.

SUMMARY

An inspection apparatus for a composite end portion of a part, the part having a contact surface and opposed first and second part surfaces, may include a first member having a first contact element and a second member having a second contact element. The second member may be movably connected to the first member. The first and second members may be shaped to define a gap sized to receive the composite end portion such that the composite end portion is disposed between the first and second members when the composite end portion is received within the gap. When the composite end portion is received in the gap the first contact element may be configured to contact the first part surface and the second contact element may be configured to contact the second part surface. The apparatus may include at least one ultrasonic array supported by at least one of the first and second members. The at least one ultrasonic array may be configured to transmit ultrasonic waves toward the composite end portion when the composite end portion is received in the gap. The apparatus may include a fluid conduit through one of the first and second members. The fluid conduit may have a first end configured to be coupled to a suction system. A second end of the fluid conduit may be configured to be adjacent to the contact surface when the composite end portion is received in the gap.

A method of inspecting a composite end portion of a part, the part having a contact surface and opposed first and second part surfaces, may include positioning an inspection apparatus such that the composite end portion is received in a gap of the inspection apparatus. So positioned, a first contact element of the inspection apparatus may contact the first part surface, a second contact element of the inspection apparatus may contact the second part surface, and a second end of a fluid conduit of the inspection apparatus may be adjacent to the contact surface. The method may include activating a suction system fluidly connected to a first end of the fluid conduit to draw the contact surface toward the second end. The method may include transmitting ultrasonic waves from at least one ultrasonic array of the inspection apparatus into the part and detecting ultrasonic waves with the at least one ultrasonic array. The method may include moving the inspection apparatus along the composite end portion.

A system for inspecting composite end portion of a part, the part having a contact surface and opposed first and second part surfaces, may include a robotic arm, a controller assembly configured to control the robotic arm, and an inspection apparatus coupled to the robotic arm. The inspection apparatus may include a first member having a first contact element and a second member having a second contact element. The second member may be movably connected to the first member. The first and second members may be shaped to define a gap sized to receive the composite end portion such that the composite end portion is disposed between the first and second members when the composite end portion is received in the gap. When the composite end portion is received in the gap, the first contact element may be configured to contact the first part surface and the second contact element may be configured to contact the second part surface. The inspection apparatus may include at least one ultrasonic array supported by at least one of the first and second members. The at least one ultrasonic array may be configured to transmit ultrasonic waves toward the composite end portion when the composite end portion is received in the gap. The inspection apparatus may include a fluid conduit through one of the first and second members, the conduit having first and second ends. The first end may be configured to be coupled to a suction system. The second end may be configured to be adjacent to the contact surface when the composite end portion is received in the gap.

A reflector assembly for inspecting a composite end portion including a bevel surface of a part, the part having opposed first and second part surfaces, may include a reflector plate having a base and an angled reflecting surface. The reflector assembly may include a support assembly attached to the base and configured to support the reflector plate on the first part surface. So supported, the base and the angled reflecting surface may be adjacent to the first part surface and the bevel surface, respectively. The angled reflecting surface may be configured to reflect ultrasonic waves transmitted from an ultrasonic array and through the bevel surface when (a) the support assembly supports the reflector plate on the first part surface, (b) the ultrasonic array is placed adjacent to the second part surface, (c) the reflector assembly, the composite end portion, and the ultrasonic array are submerged in liquid, and (d) the ultrasonic array transmits ultrasonic waves through the bevel surface.

A method of inspecting a composite end portion, including a bevel surface, of a part, the part having opposed first and second part surfaces, may include positioning an ultrasonic array adjacent to the second part surface and positioning a reflector assembly on the first part surface adjacent to the composite end portion. The method may include submerging the ultrasonic array, the reflector assembly, and the composite end portion in liquid. The method may further include transmitting ultrasonic waves from the ultrasonic array into the part, reflecting ultrasonic waves transmitted from the ultrasonic array via the reflector assembly, and detecting ultrasonic waves with the ultrasonic array. The method may include moving the ultrasonic array along the composite end portion.

The present disclosure provides various apparatuses, systems, and methods of use thereof. In some embodiments, an apparatus may include first and second members sized to receive a composite end portion of a part in a gap between the first and second members and at least one ultrasonic array. In some embodiments, an apparatus may include a filler element having a first filler surface configured to complementarily match a bevel surface of the composite end portion. In some embodiments, an apparatus may include a reflector plate configured to reflect ultrasonic waves directly back to a bevel surface of the composite end portion. In some embodiments, an apparatus may be configured to inspect the composite end portion when the composite end portion and at least a portion of the apparatus are both submerged in water.

Features, functions, and advantages may be achieved independently in various embodiments of the present disclosure, or may be combined in yet other embodiments, further details of which can be seen with reference to the following description and drawings.

DESCRIPTION

Overview

Various embodiments of apparatuses, systems, and methods for inspecting a composite end portion of a part are described below and illustrated in the associated drawings. Unless otherwise specified, the apparatus, system or method and/or their various components may, but are not required to, contain at least one of the structure, components, functionality, and/or variations described, illustrated, and/or incorporated herein. Furthermore, the structures, components, functionalities, and/or variations described, illustrated, and/or or incorporated herein in connection with the present teachings may, but are not required to, be included in other similar inspection apparatuses, system, or methods. The following description of various embodiments is merely exemplary in nature and is in no way intended to limit the disclosure, its application, or uses. Additionally, the advantages provided by the embodiments, as described below, are illustrative in nature and not all embodiments provide the same advantages or the same degree of advantages.

Examples, Components, and Alternatives

The following sections describe selected aspects of exemplary apparatuses, systems, and methods for inspecting parts as well as related systems and/or methods. The examples in these sections are intended for illustration and should not be interpreted as limiting the entire scope of the present disclosure. Each section may include one or more distinct inventions, and/or contextual or related information, function, and/or structure.

Example 1

Figure 1:
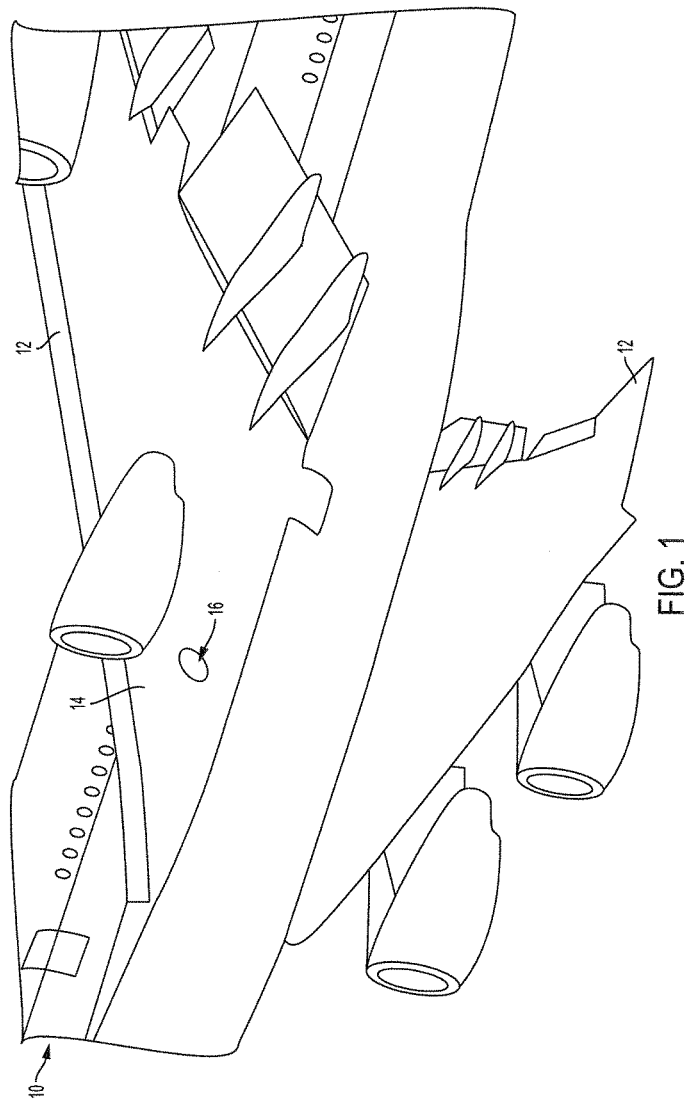
FIG. 1 is a schematic perspective view of a portion of the underside of an aircraft showing a wing access hole in an under surface of an aircraft wing.
Figure 2:
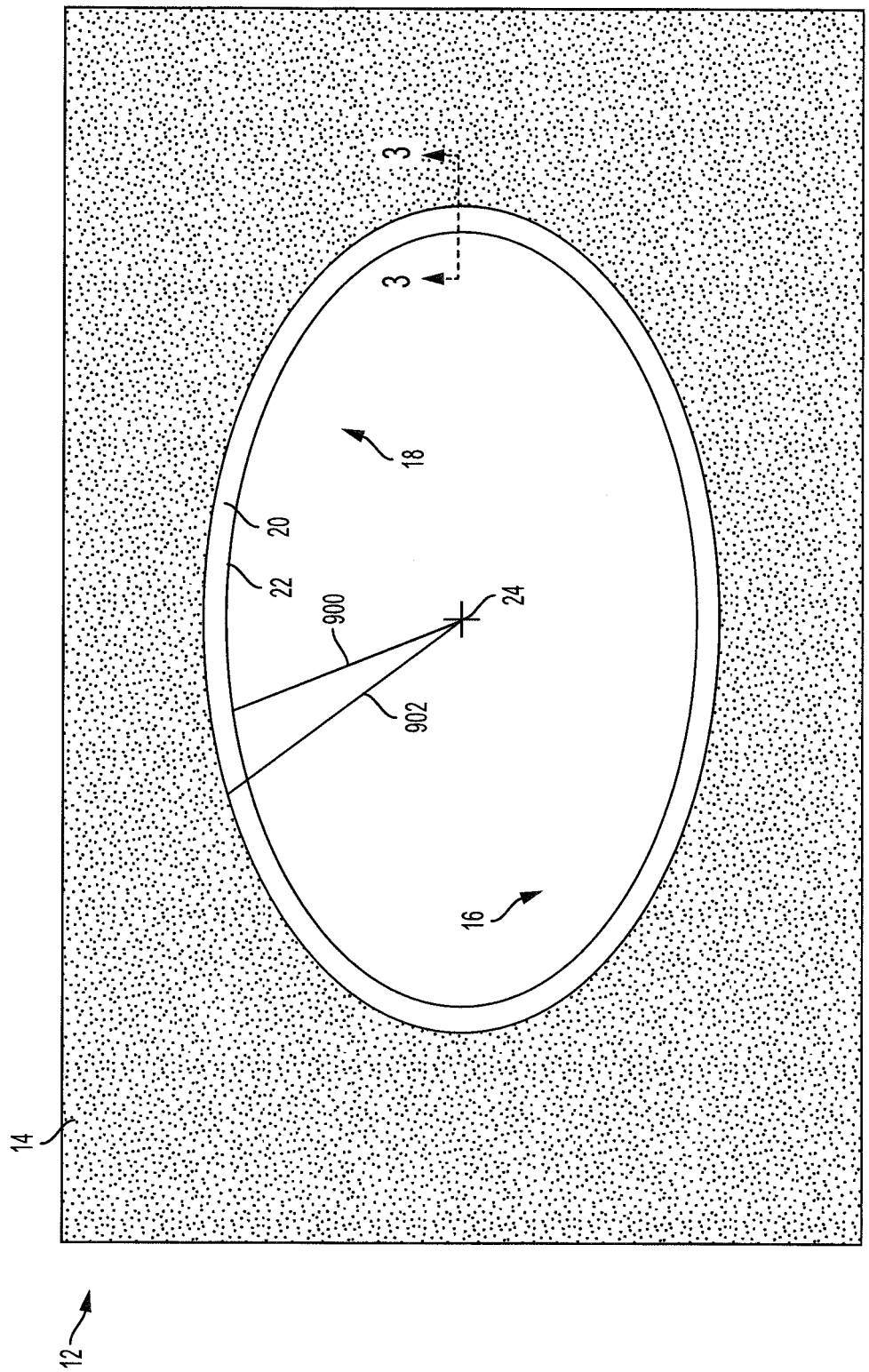
FIG. 2 is a schematic view of the wing access hole of FIG. 1 showing a chamfered edge of the hole.
Figure 3:
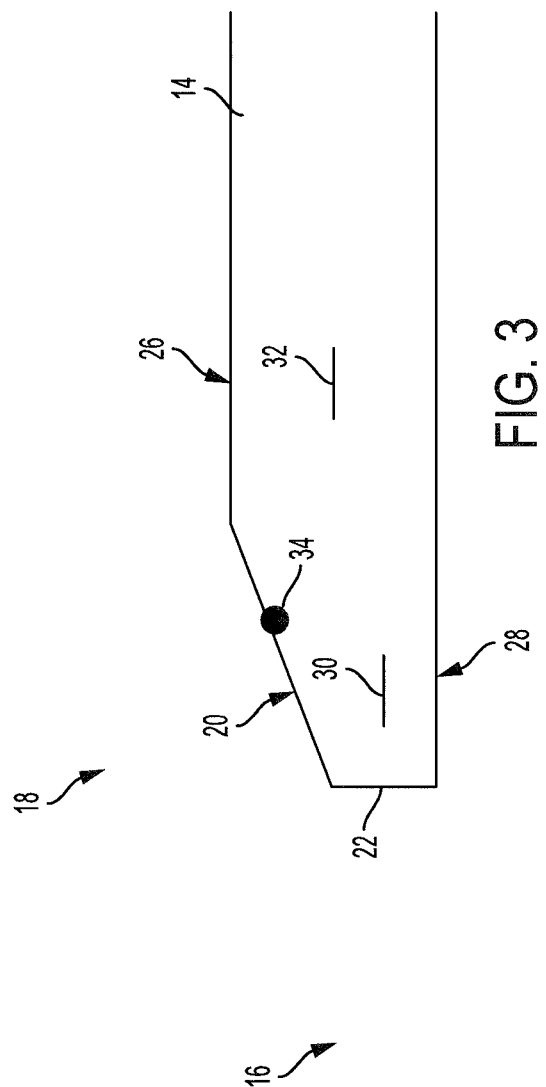
FIG. 3 is a schematic cross-sectional view of a portion of an edge of the wing access hole of FIG. 1, taken at 3-3 in FIG. 2.

This example describes an illustrative composite end portion of a part, as shown in FIGS. 1-3.

FIG. 1 is a schematic perspective view of an aircraft, generally indicated at 10. The wings 12 of aircraft 10 may be constructed, at least partially, of composite materials. For example, a portion of wing skin 14 on an under side of a wing 12 may be a composite material. The wing skin 14 may initially be formed as a large single piece and subsequently altered as it is incorporated into the rest of the wing structure. For example, one or more access holes 16 may be cut into the wing skin on an underside of the wing. These holes may give technicians access to the interior space of the wing during construction or afterwards.

FIG. 2 is a schematic view of a wing access hole 16, as viewed from outside the wing 12. Access hole 16 is depicted as having an oval shape in FIG. 2, however, any shape hole may be appropriate depending on the intended use of the access hole. Access hole 16 may be defined by an edge or end portion 18 of the wing skin 14.

The edge of the wing skin may be beveled, radiused, chamfered, or otherwise trimmed to create a trimmed face 20. The trimmed face 20 may extend from an inner distance 900 proximate a distal end 22 of the wing skin to an outer distance 902, the inner and outer distances measured from a center 24 of access hole 16. As the access hole may have an oval shape, the inner distance 900 and the outer distance 902 may not be constant around the perimeter of the hole. Outer distance 902 may be larger than inner distance 900 at all locations around the perimeter of the hole. The difference between the outer and inner distances may be constant around the perimeter of the hole.

FIG. 3 is a schematic cross-sectional view of the wing skin 14, taken at 3-3 in FIG. 2. Wing skin 14 may have an outer surface 26 and an inner surface 28. The outer surface 26 and the trimmed face 20 may be viewable from a vantage point outside the aircraft wing. Inner surface 28 may be viewable from a vantage point within an interior of the aircraft wing.

As described above, delaminations or other defects may occur within structures, such as wing skin 14. These may occur during creation of the wing skin, during cutting of hole 16, or during trimming and creation of trimmed face 20. Defects may occur relatively close to the distal end 22 of the wing skin, for example delamination 30, or relatively farther away from the trimmed face and within the wing skin, for example delamination 32. These defects may occur within the bulk of the wing skin or on a surface of the wing skin, for example as a hole 34 on trimmed face 20.

Example 2

This example describes an illustrative system for inspecting a composite end portion of a part. The illustrative system may include an illustrative inspection apparatus, see FIG. 4.

Figure 4:
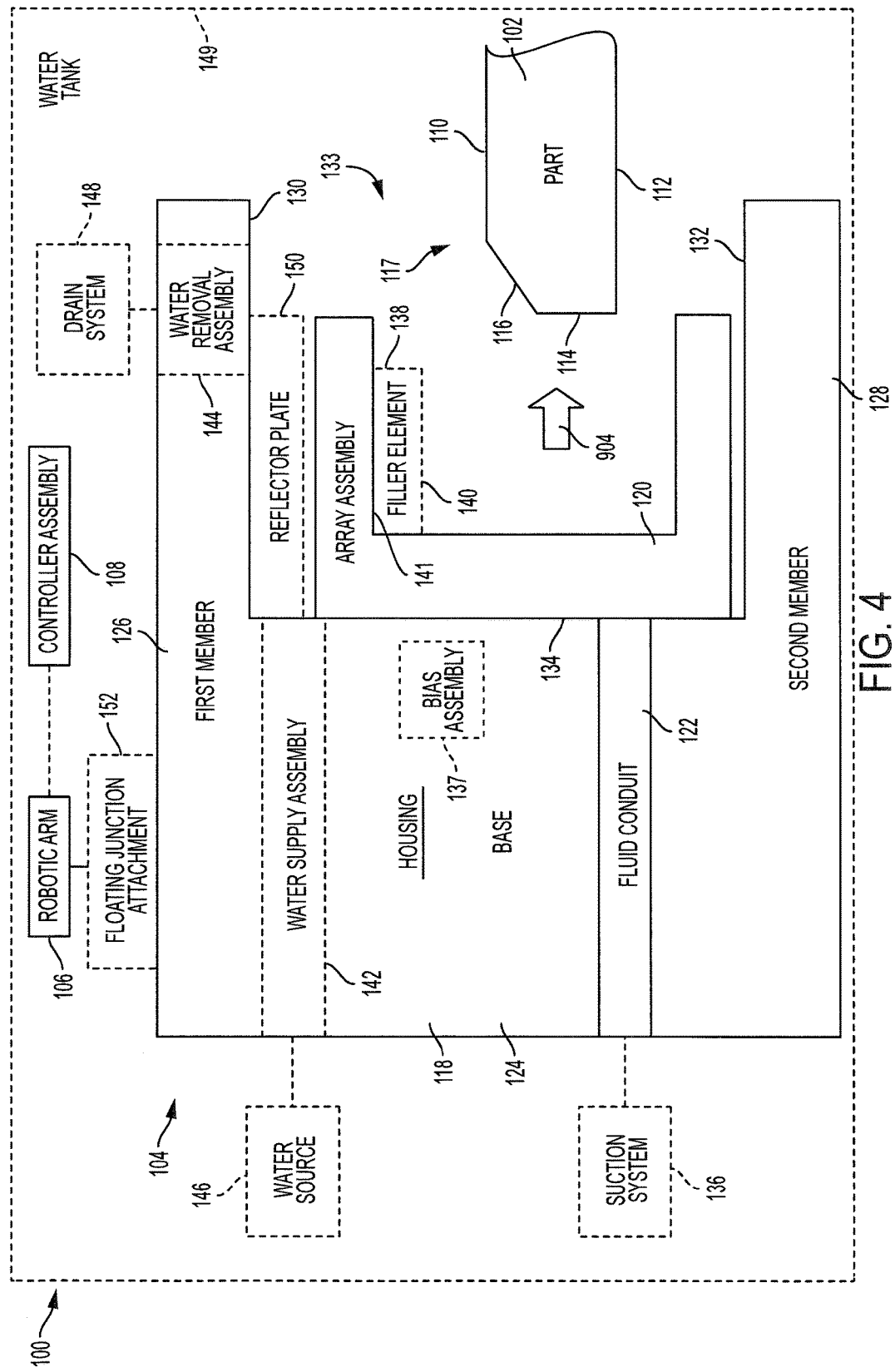
FIG. 4 is a block diagram of an illustrative system, including an illustrative apparatus, and an illustrative part.

FIG. 4 is a block diagram of an illustrative inspection system, generally indicated at 100. Inspection system 100 may be used to inspect a part 102. System 100 may include an inspection apparatus, generally indicated at 104, a robotic arm 106, and a controller assembly 108.

Part 102 may be made of a composite material, such as a plurality of reinforcing fibers bound by a matrix material. Part 102 may also be made of other materials, such as one or more metals, and/or one or more other hybrid materials, such as titanium graphite. The part 102 may have a first part surface 110, second part surface 112, an end or contact surface 114 and a bevel surface 116. An example of such a part may be the wing skin 14 described in Example 1 above, though inspection system 100 may be used for a wide variety of parts in many different contexts. The first part surface need not be parallel to the second part surface. The first and second part surfaces may not be inside or outside a particular object, but may simply label two different sides of an object.

Bevel surface 116 is depicted as a flat surface but many different shapes and curvatures are conceivable. For example, trimmed face 20 in Example 1 is nearly flat, yet may have a small degree of curvature as it forms a portion of the perimeter of an oval-shaped hole. Other examples of bevel surface 116 may have a rounded or radiused shape. Part 102 may have been trimmed from a larger shape into the shape depicted in FIG. 4, or it may have been formed in this shape through some curing process. Together, the bevel surface 116 and the end surface 114, along with portions of the first and second part surface proximate the bevel surface and end surface, may be taken to be a composite end portion 117.

Inspection apparatus 104 may include a housing 118, at least one ultrasonic array or array assembly 120, and a fluid conduit 122. The housing may carry the at least one ultrasonic array and the fluid conduit. The housing may be configured to attach to the composite part 102, as indicated by arrow 904, and maintain that attachment via the fluid conduit 122. While attached to the part, the at least one ultrasonic array 120 may emit ultrasonic sound waves into or toward the part in order to scan the part for defects.

Housing 118 may include a base 124, a first member 126 extending from the base along the first part surface 110 of the part, and a second member 128 extending from the base along the second part surface 112 of the part. The first member may have first contact element 130 configured to abut or otherwise couple with the first part surface of the part. The second member may have second contact element 132 configured to abut or otherwise couple with the second part surface of the part. The base may be configured to abut or otherwise couple with the end surface 114 of the part.

The first and second members may be shaped to define a gap 133. Gap 133 may be sized to receive the composite end portion 117 such that the composite end portion is disposed between the first and second members when the composite end portion is received in the gap.

The base, first member, and second member of the housing may be formed of one unitary piece or more than one piece. For example, the base, first member, and second member may be three separate pieces operatively coupled together. In another example, a first portion of the base may be formed unitarily with the first member and a second portion of the base may be formed unitarily with the second member. That is, the housing may be substantially formed by the first and second members. Such two pieces may be operatively coupled together, for example, via a hinge, via a spring mechanism, or any other appropriate means. The housing 118 may be configured to clamp down on the part 102, like the jaws of a crescent wrench or a clamshell.

The at least one ultrasonic array assembly 120 may include one or more than one ultrasonic array. Any of the one or more ultrasonic arrays may be a linear array or a linear phased array. Any of the one or more ultrasonic arrays may be configured to emit ultrasonic sound waves, detect ultrasonic sound waves, or emit and detect ultrasonic sound waves. In the case where only one ultrasonic array is used, that array may be disposed proximate the second part surface 112, the first part surface 110, the end surface 114 or the bevel surface 116 of the part 102. In the case where more than one ultrasonic array is used, the arrays may be disposed proximate different sides, surfaces, or faces of the part.

The fluid conduit 122 may be carried by the housing and fluidly connected to an inner surface 134 of the base. The fluid conduit may have a first end configured to be coupled to a suction system 136 and a second end configured to be adjacent the contact surface 114 when the composite end portion is received in the gap. The second end of the fluid conduit may be on the inner surface 134 of the base. The suction system 136 may include any suitable structure configured to cause fluid, such as water or air, to enter the fluid conduit at the second end on the inner surface of the base and flow through the fluid conduit. For example, the suction system may include a pump, a vacuum source, and/or other suitable structure configured to draw fluid through the fluid conduit. This may cause a force or suction effect which may draw the inspection apparatus 104 toward the part 102.

When the inspection apparatus 104 is attached to the part 102, the end surface 114 of the part may abut the inner surface 134 of the base proximate the second end of the fluid conduit 122. The suction system 136 may create a pressure differential between an interior space between the housing and the part and an exterior space outside the housing which may thereby maintain attachment between the inspection apparatus and the part. The housing, in particular the inner surface 134 of the base, the first contact element 130, and the second contact element 132, along with the fluid conduit may be configured so that the inspection apparatus maintains contact with the part as the apparatus is translated along the composite end portion of the part.

Inspection apparatus 104 may optionally include a bias assembly 137. Bias assembly 137 may be configured to exert a force or forces between the first member 126 and the second member 128, thereby drawing the first and second members toward one another. The bias assembly may allow the inspection apparatus to clamp down on the composite part when the apparatus is attached to the part. The bias assembly may include one or more springs configured to impel the first and second members toward one another. Alternately, the bias assembly may include a pump configured to create a vacuum or region of lower pressure in an interior space of the housing, relative to the pressure outside the housing. This pressure differential may result in a net force on the first and second members toward one another.

Thus, the housing, bias assembly, and fluid conduit may be configured so that the inspection apparatus self-aligns with the composite part. That is, by virtue of attaching to the part, the at least one ultrasonic array and other components may be aligned properly for inspection of the part without further alignment from outside the inspection apparatus.

Inspection apparatus 104 may optionally include a filler element 138. The filler element may have a first filler surface 140 configured to match the bevel surface 116 of the part. That is, the first filler surface 140 of the filler element may make a complementary fit with the bevel surface 116 of the part 102. In some cases, the filler element may be shaped and sized so as to fill a portion of a void created when the part was trimmed to create bevel surface 102. If the bevel surface has a convex curvature, then the first filler surface may have a corresponding concave curvature. The filler element may have a second filler surface 141. The filler element may be configured to continue the first part surface 110 of the part 102. That is, the second filler surface 141 may be co-planar with the first part surface when the composite end portion is received in the gap.

The filler element may be made of substantially the same material as the part 102. Alternately, the filler element may be made of a different material but having substantially the same acoustic impedance as the part 102. So configured, the speed of ultrasonic sound waves may be the same in the filler element 138 and the part 102. Sound waves that travel across a boundary between the filler element and the part may then not be refracted, even if the sound waves encounter the boundary at an oblique angle. That is, sound waves may travel across the boundary in a straight line ray without bending as they cross the boundary.

In the case where the filler element 138 is included in inspection apparatus 104, the filler element may be disposed between one of the at least one ultrasonic arrays 120 and the bevel surface of the part 102. The ultrasonic array 120 may be configured to extend beyond the filler element 138 over the first part surface 110 of the part when the inspection apparatus is attached to the part. The filler element may be configured to continue the first part surface. In such a configuration, the ultrasonic array may simultaneously direct ultrasonic sound waves into the filler element 138 and the part 102 through the first part surface 110 of the part.

Coupling ultrasonic sound waves into and out of the part and/or the filler element 138 may be aided by a layer of water disposed between the filler element and the part 102, between the at least one ultrasonic array 120 and the filler element, and between the at least one ultrasonic array and the part. When the composite end portion is received in the gap, the first filler surface 140 and the bevel surface 116 may form a first channel therebetween. Further, the at least one ultrasonic array 120 and the second filler surface 141 may form a second channel therebetween. The second channel may include first and second sides. When the composite end portion is received in the gap the first side may be formed by the second filler surface and the first part surface, and the second side may be formed by the at least one ultrasonic array. The first and second channels may be filled with water.

In the case where the inspection apparatus is configured to be used in an environment where the apparatus and the part are not submerged in water, a water supply assembly 142 and a water removal assembly 144 may be included in inspection apparatus 104.

The water supply assembly 142 may include a fluid inlet which may be in fluid communication with the inner surface 134 of the base 124. The inspection system 100 may include a water source 146 coupled to the fluid inlet of the water supply assembly 142. The water source may include a water reservoir, a pump, and any necessary filters. Together, the water source 146 and the water supply assembly 142 may introduce water into an interior space of the housing proximate the bevel surface 116 of the part, the first part surface 110 of the part, the end surface 114 of the part, and/or the second part surface 112 of the part, the filler element 138, and the ultrasonic array. That is, the water supply assembly may introduce water into the first and second channels. Water supply assembly 142 may include one or more valves configured to control the flow of water through the assembly and into the interior space of the housing.

The first channel may include first and second end portions and the second channel may include third and fourth end portions. The fluid inlet of the water supply assembly may receive a fluid, such as water, and may be fluidly connected to the first and third end portions.

The water removal assembly 144 may have a fluid outlet in fluid communication with an interior space of the housing 118. The inspection system 100 may include a drain system 148 coupled to the fluid outlet of the water removal assembly 144. The drain system may include a reservoir, a pump, and any necessary filters. Water may travel from the water source system 146, through the water supply assembly 142 into an interior space of the housing and around or by the filler element 138, the at least one ultrasonic array 120, and the part 102, out of the interior space of the housing through the water removal system 144, and discharged into the drain system 148. The fluid outlet may be fluidly connected to the second and fourth end portions of the first and second channels. In some cases, the water source may be coupled to the drain system so that together they form a closed water source and drain system.

In some embodiments, the inspection apparatus 104 may be configured to be used in an environment where the composite end portion of the part and at least a portion of the apparatus are both submerged in water. For example, the inspection apparatus 104, portions of the composite part 102, and one or more elements of the inspection system 100 may be configured to be used when submerged in a water tank 149 or some other such container. The water inherent to such an environment may serve to help couple the ultrasonic sound waves into and out of the part 102. In this case, certain elements of the water supply 146, the water supply assembly 142, the water removal assembly 144, and the drain system 148 may not be necessary. The fluid inlet of the water supply assembly 142 may include an aperture which may be configured to allow liquid to enter the first and second channels when the apparatus is submerged.

In some embodiments the inspection apparatus 104 may include a reflector plate 150. When the inspection apparatus is attached to the composite part 102 the reflector plate 150 may be disposed proximate the bevel surface 116 of the part. The reflector plate may be spaced from the bevel surface and may include an angled portion disposed at an angle relative to the bevel surface. The reflector plate may include a second portion disposed proximate the first part surface 110. The second portion of the reflector plate 150 may be spaced from the first part surface and be oriented substantially parallel to the first part surface of the part. In the case when the reflector plate is included in inspection apparatus 104, the array assembly 120 may be disposed primarily proximate the second part surface 112 and not the first part surface 110, when the part is received within the gap 133. That is, the array assembly may not be disposed between the reflector plate and the part.

The following cases describe configurations where the inspection apparatus 104 includes the reflector plate 150 and the part is inspected in a submerged environment. The at least one ultrasonic array 120 and the reflector plate may be configured so that ultrasonic sound waves are first sent into, through, and out of the part 102, reflected off of the reflector plate, directed back into, through and out of the part, and finally detected by the at least one ultrasonic array. More specifically, ultrasonic waves may be emitted by the at least one ultrasonic array proximate the second part surface 112 of the part, travel through a layer of water, enter the part through the second part surface, travel through the bulk of the part, exit the part into a layer of water through one or both of the bevel surface 116 or the first part surface 110, reflect off the reflector plate, travel back through the layer of water, into the part through one or both of the bevel surface or the first part surface, exit the part into the layer of water through the second part surface, and be detected by the at least one ultrasonic array. Subsequent analysis of the emitted and detected signals may then provide information about the defects in the part.

Inspection apparatus 104 may include a floating attachment junction 152. The floating attachment junction may be configured for attachment to the robotic arm 106. The floating attachment junction may allow the robotic arm to move with respect to the housing 118 of the inspection apparatus while maintaining the attachment between the robotic arm and the inspection apparatus. That is, there may be a degree of "play" or freedom of movement in the coupling between the robotic arm and the floating attachment junction. The floating attachment junction may sometimes be referred to as a "coupler assembly."

As described above, the inspection apparatus may be self-aligning as it attaches to the part 102. In such a case, the robotic arm may position the inspection apparatus relatively close to where the apparatus would need to be in order to inspect the part. Using the freedom of movement in the floating attachment junction 152, the inspection apparatus itself may then complete the alignment of the apparatus in order to begin inspection. The robotic arm could then move the inspection apparatus along the composite end portion of the part, under the direction of the controller assembly 108, while the inspection apparatus maintains correct alignment with the part.

Robotic arm 106 may be controlled via controller assembly 108. Controller assembly 108 may direct the robotic arm 106 on pre-programmed routes, may allow a user to direct the robotic arm, or a combination of the two. With the above-described self-aligning property of inspection apparatus 104 and the floating attachment junction 152, pre-programmed routes may not need to be particularly well-defined, both in the position of the inspection apparatus and the orientation of the inspection apparatus relative to the part.

Alternately, the robotic arm 106 and the controller assembly 108 may be omitted from the inspection system 100. In such a case, the inspection apparatus 104 may be moved along composite part by hand or some other translation mechanism.

Example 3

Figure 5:
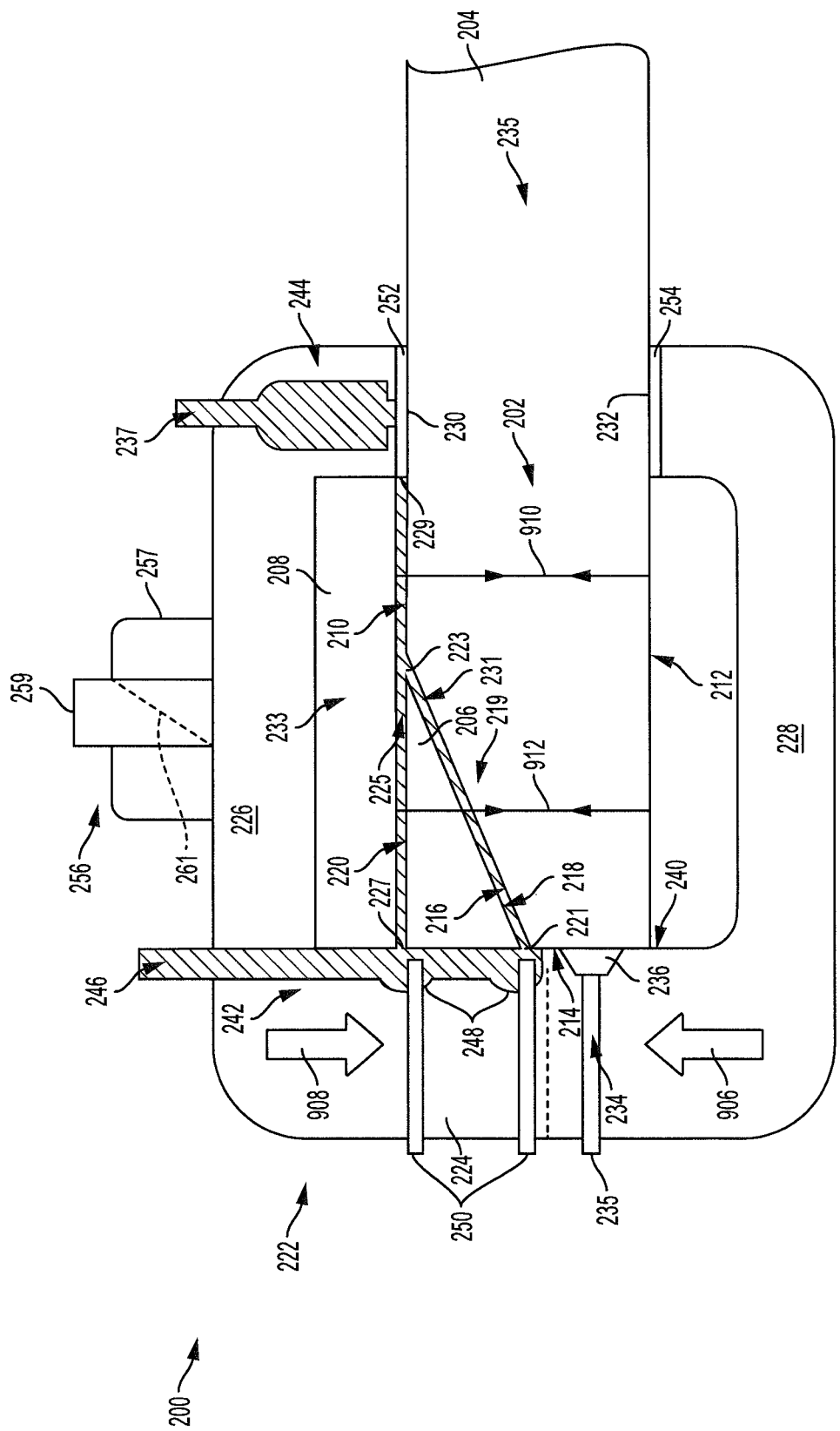
FIG. 5 is a schematic cross sectional view of an illustrative apparatus including a filler element, and an illustrative part.
Figure 6:
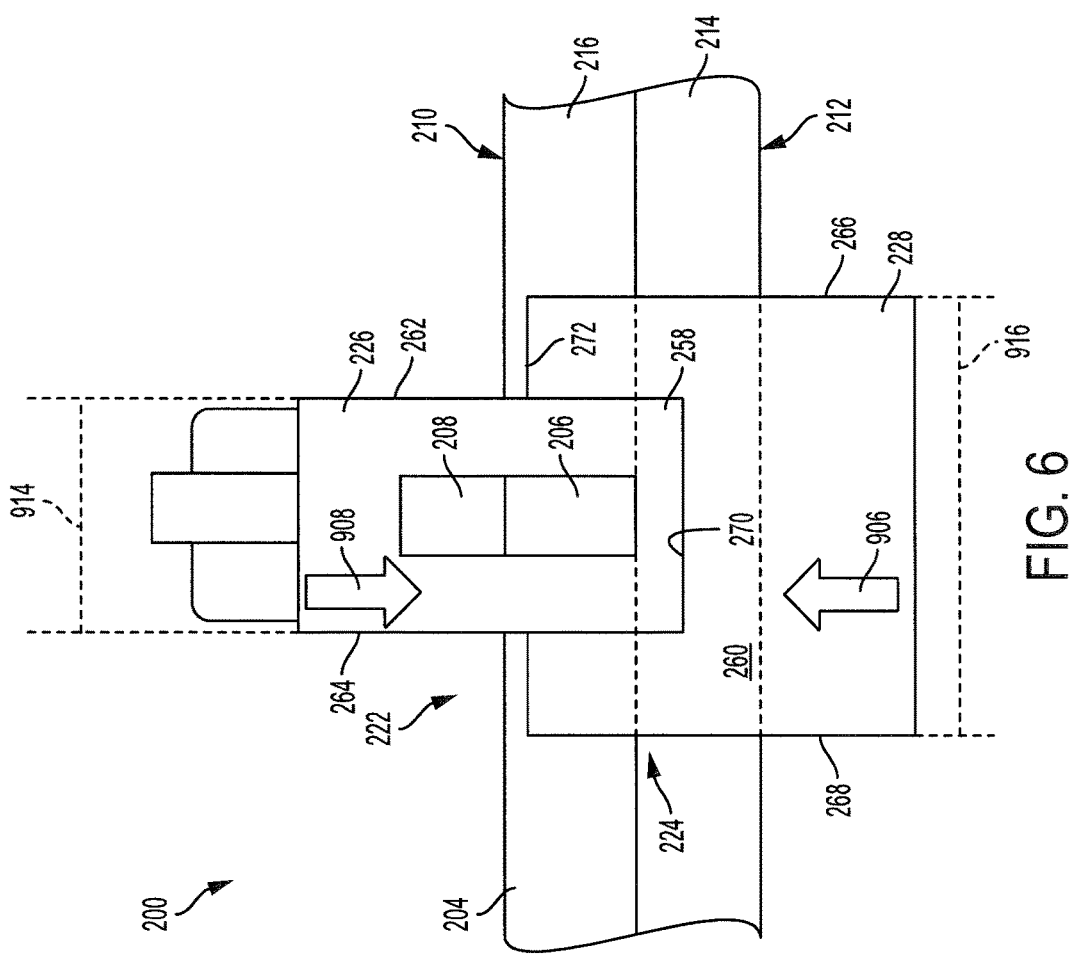
FIG. 6 is a schematic end view of the illustrative apparatus of FIG. 5 and an illustrative part.
Figure 7:
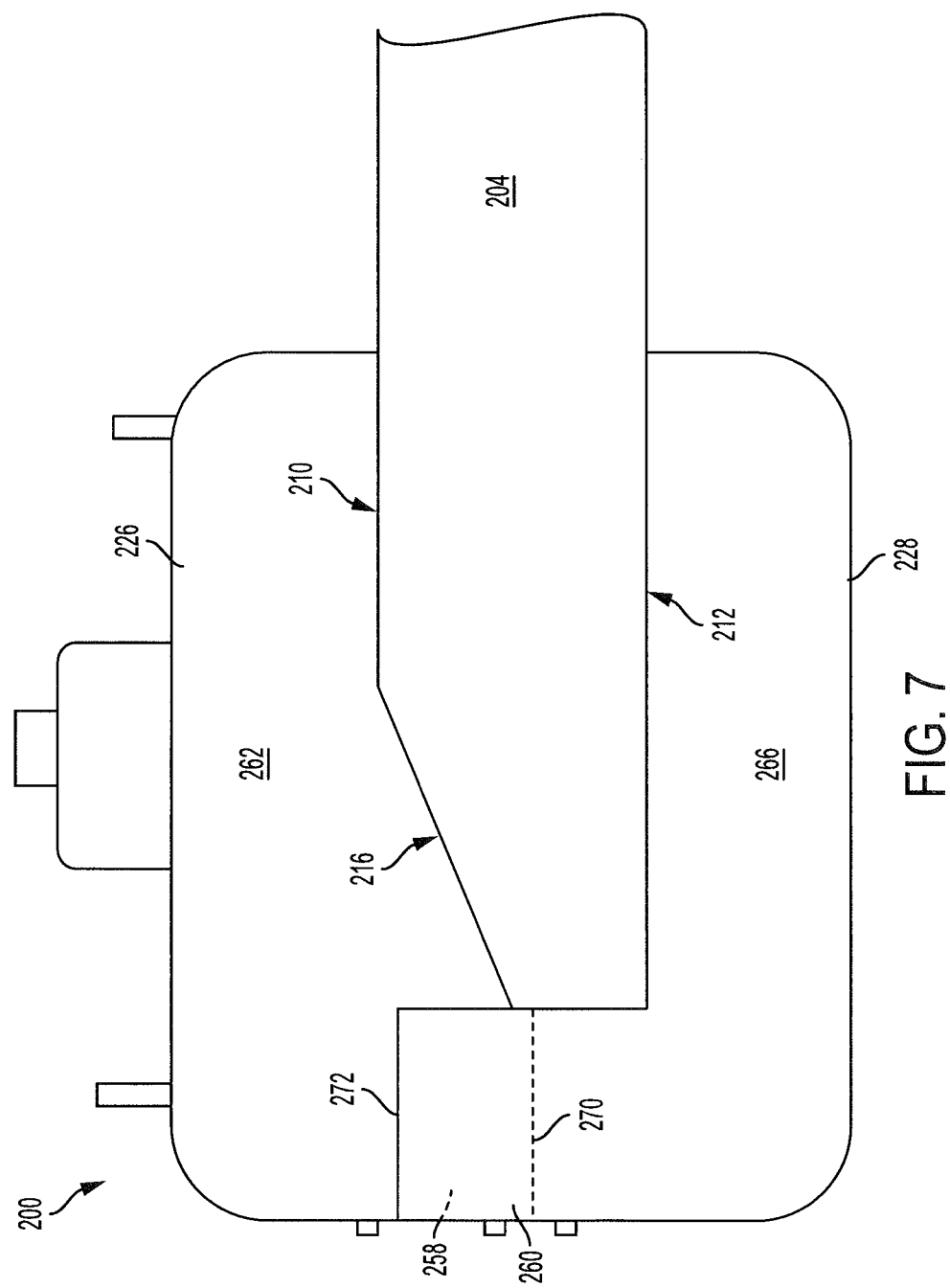
FIG. 7 is a schematic side view of the illustrative apparatus of FIG. 5 and an illustrative part.

This example describes an illustrative inspection apparatus for inspecting an edge of a composite part, see FIGS. 5-7.

FIG. 5 is a schematic cross sectional view of an embodiment of an illustrative apparatus, generally indicated at 200. Apparatus 200 may be used to inspect a trimmed edge or composite end portion 202 of a part 204. Apparatus 200 may include a filler element 206 and an ultrasonic array 208.

The part 204 may be similar to wing skin 14 described in Example 1 or part 102 described in Example 2. Part 204 may include a first part surface 210, a second part surface 212, an end or contact surface 214, and a bevel surface 216. Together, the bevel surface, the end surface, and portions of the first and second part surfaces proximate the bevel surface and the contact surface may be considered as the composite end portion 202.

Filler element 206 may be similar to filler element 138 described in Example 2. Filler element 206 may be of a similar material to the part 204. The filler element may be of a different material than part 204 and yet have sound waves travel at a similar speed as those that travel through the part. That is, the filler element and the part may have the same acoustic impedance.

The filler element may have a first filler surface 218 configured to match the bevel surface 216 of the part. The filler element may be disposed so that the first filler surface is spaced from the bevel surface in order that a layer of water may fill the space between the filler element and the part. That is, the first filler surface may form a first channel 219 with the bevel surface when the apparatus is attached to the part. The first channel may include a first end portion 221 and a second end portion 223.

The filler element 206 may be configured to continue the first part surface 210 of the part 204. That is, the filler element may have a second filler surface 220 that may continue the first part surface of the part when the apparatus 200 is attached to the part 204, with the possible exception of a gap between the filler element and the part for the flow of water between the filler element and the part.

Ultrasonic array 208 may be similar to the array assembly 120 described in Example 2. Ultrasonic array 208 may be a linear array or a linear phased array. The ultrasonic array may include ultrasonic sound wave emitters and ultrasonic sound wave detectors. The array may be disposed over the filler element 206 and a portion of the first part surface 210 of the part when the apparatus 200 is attached to the part 204.

The array may be spaced from the filler element and the first part surface of the part so that a layer of water is disposed between the ultrasonic array and the filler element and between the ultrasonic array and the part. That is, the ultrasonic array may form a second channel 225 with the second filler surface and, optionally, a portion of the first part surface 210. The second channel may have a third end portion 227 and a fourth end portion 229. The second channel may have a first side 231 and a second side 233. When the apparatus is attached to the part, the first side may be formed by the second filler surface and the first part surface and the second side may be formed by the at least one ultrasonic array.

Apparatus 200 may include a housing 222 which may be similar to housing 118 described in Example 2. Housing 222 may include a base 224, a first member 226, a second member 228, a first contact element 230, and a second contact element 232, all of which may be similar to the similarly numbered components of housing 118. The housing may be configured to carry the filler element 206 and the ultrasonic array 208. The first and second members may be shaped to define a gap 235 sized to receive the composite end portion 202. Gap 235 may be similar to gap 133 described in Example 2.

Apparatus 200 may include a fluid conduit 234 which may be similar to the fluid conduit 122 described in Example 2. The fluid conduit may extend through one of the first and second members and may have a first end 235 and a second end 236. The first end may be configured to be coupled to a suction system. The second end may be configured to be adjacent to the contact surface 214 when the composite end portion 202 is received in the gap. The suction system may be configured to draw air from the second end 236, thereby producing a suction force which may impel the inner surface 240 of the base against the contact surface 214 of the part 204

Apparatus 200 may include a water supply assembly 242 and a water removal assembly 244. These components may be similar to the water supply assembly 142 and the water removal assembly 144, respectively, described in Example 2. The water supply assembly 242 may include a fluid inlet 246. The fluid inlet may be fluidly connected to one or more input ports 248 disposed on an interior surface of the housing. The flow of water through the fluid inlet and out through the input ports may be regulated by one or more control pins 250. The fluid inlet may be fluidly connected to the first end portion 221 of the first channel 219 and the third end portion 227 of the second channel 225.

Thus, water may flow from a water source, through the water supply assembly 242 and into apparatus 200. Inside apparatus 200, water may fill spaces, gaps, channels, or voids between the bevel surface 216 of the part 204 and the first filler surface 218 of the filler element 206, between the filler element and the ultrasonic array 220, and between the ultrasonic array and the upper surface 212 of the part, among others. These layers of water between the various components may aid in the transit of ultrasonic waves between the various components.

Water removal assembly 244 may remove water from the apparatus at the same rate at which the water supply assembly introduces water to the apparatus. Alternately, the water supply removal system may remove water at a slower rate than the water introduction rate to account for losses of water from the system. Water removal assembly 244 may include a fluid outlet 237 for discharging the fluid. Fluid outlet 237 may be fluidly connected to the second end portion 223 of the first channel 219 and to the fourth end portion 229 of the second channel 225.

The first member 226 and the second member 228 of the housing 222 may be drawn by a force or forces toward one another by a bias assembly, such as bias assembly 137 described in Example 2. The attractive forces are indicated by arrows 906 and 908. This biasing force or forces may be created by spring(s), bias element(s), or via a vacuum system. For example, the suction system which may cause the inner surface 240 of the base 224 to abut the contact end 214 of the part may also create a lower pressure within the apparatus. The lower pressure may act with the pressure outside the apparatus to create forces along the directions 906 and 908, thereby causing the first and second members to clamp down on the part. In the case where one or more springs are used to create the biasing forces 906 and 908, the springs may be configured to work along with one or more hinges. These hinges may have an open position which allows for positioning of the apparatus proximate the part and a closed position where the apparatus attaches to the part and the composite end portion is received within the gap.

The first contact element 230 of the first member 226 may include a low-friction pad 252. Pad 252 may be made of Teflon PTFE or some other material capable of providing an effective seal to air and/or water and allowing apparatus 200 to slide along part 204. The second contact element 232 of the second member 228 may include a similar low-friction pad 254. The low-friction pads 252 and 254 may substantially seal an interior space between the housing 222 and the part to the ingress and egress of air and water.

Apparatus 200 may be transported along the trimmed edge of the part by a robotic arm, such as robotic arm 106 described in Example 2. Apparatus 200 may attach to the robotic arm via a floating attachment junction 256. The floating attachment junction 256 may be similar to floating attachment junction 152 described in Example 2.

Floating attachment junction 256 may sometimes be referred to as "coupling assembly 256." The coupling assembly may include a first coupler 257, a second coupler 259, and at least one bias element 261. The first coupler may be attached, such as fixedly attached, to one of the first and second members. In some examples, the first coupler may be formed with the first member or the second member. The second coupler may be attached to the first coupler and may be configured to move relative to the first coupler along at least two axes (or at least three axes), which may be orthogonal, non-orthogonal, and/or other suitable axes. The second coupler may be configured to be attached or coupled to a robotic arm. The at least one bias element may be configured to urge the second coupler toward a nominal position when the second coupler is moved away from the nominal position. The nominal position may include any suitable position, such as a center or equilibrium position.

To inspect the part 204 for delaminations, holes, and other defects, apparatus 200 may emit ultrasonic sound waves from the ultrasonic array 208 and detect ultrasonic sound waves with the ultrasonic array after they have passed through the part.

Ultrasonic array 208 may emit ultrasonic sound waves substantially all along the length of the array. The emitted sound waves may travel directly away from the array, for example in the view of FIG. 5, down. The emitted sound waves may be represented by one or more representative rays, for example, representative rays 910 and 912 in FIG. 5. Alternately, in the case where a phased array is used, the emitted sound waves may not travel perpendicularly to the array but rather at an angle with respect to the array.

Ray 910 may travel from the ultrasonic array, through a layer of water adjacent the array, and into the composite-material part 204 through the first part surface 210 of the part. Ray 910 may reflect off the second part surface 212 of the part and travel back through the bulk of the part. If the ultrasonic array is aligned parallel to the first part surface, and the second part surface is aligned parallel to the first part surface, then the reflected ray may travel back along the same path along which it initially traversed the bulk of the part. The ray 910 may then leave the part through the first part surface, again travel through the layer of water adjacent the ultrasonic array, and be detected by the ultrasonic array.

Ray 912 may travel from the ultrasonic array, through a layer of water adjacent the array, and into the filler element 206 through the second filler surface 220 of the filler element. Ray 912 may then travel out of the filler element through the first filler surface face 218, through a layer of water, and into the part through the bevel surface 216. In the case where the acoustic impendences of the filler element and part are substantially the same, and the layer of water between them is thin, then ray 912 may travel between the filler element and part in a substantially straight line without bending. Ray 912 may then be reflected off of the second part surface 212 and travel back through the bulk of the part. If the ultrasonic array is aligned parallel to the second filler surface of the filler element, and the second part surface of the part is aligned parallel to the second filler surface of the filler element, then the reflected ray may travel back along the same path along which it initially traversed the bulk of the part and the filler element. The ray 912 may then leave the filler element through the second filler surface of the filler element, again travel through the layer of water adjacent the ultrasonic array, and be detected by the ultrasonic array.

By comparing the emitted sound waves to the detected sound waves a measure of the defects in the part can be found. For example, if the part is free of defects, sound waves may travel along ray 910 as described above. However, if ray 910 encounters a defect, then the sound waves may be partially scattered away from ray 910 and not be detected by the ultrasonic array. Alternately, if ray 910 encounters a defect, then the sound waves may still be reflected back to the ultrasonic array but arrive at an earlier time than if the sound waves had traveled all the way to the second part surface 212 and back to the ultrasonic array. Such an inspection apparatus may be trained on parts with known quantities or densities of defects in order to correctly interpret the detection signals from the ultrasonic array and convert those signals into detected quantities or densities of defects.

In another example, the ultrasonic array 208 may produce an image or images of the part, much as a medical ultrasound device can produce an image or images of the interior of a person's body. Defects may then be readily seen on the image or images.

Apparatus 200 may be able to simultaneously scan the composite end portion 202 of the part 204 and untrimmed portions of the part proximate the composite end portion since the ultrasonic array 208 may be configured to simultaneously send sound waves into, and receive sound waves from, the bevel surface 216 of the part and the untrimmed first part surface 210 of the part.

FIG. 6 is a schematic end view of apparatus 200 and part 204. The housing 222 is depicted as transparent, so that the filler element 206 and the ultrasonic array 208 can be seen within the housing. The bevel surface 216 can be seen proximate the contact surface 214 of the part, the first member 226 can be seen proximate the first part surface 210 of the part, and the second member 228 can be seen proximate the second part surface 212.

In the embodiment shown in FIG. 6, the base 224 is formed of two portions, a first portion 258 formed with the first member 226 and a second portion 260 formed with the second member 228. The first and second portions 258 and 260 of the base may be coupled together by one or more hinges or axels. Such an attachment may allow the apparatus 200 to have an open position where the apparatus may be positioned proximate the contact surface of the part and a closed position where the apparatus may be attached to the part and the composite end portion received within the gap. The coupling between the two portions of the base may be configured to work with a bias assembly which may impel the apparatus from the open position to the closed position, for example, by creating forces 906 and/or 908.

The first member 226 may have a width 914 and the second member 228 may have a width 916, as measured in a direction along the contact surface 214 of the part. The width 916 of the second member may be greater than the width 914 of the first member. The width 914 of the first member may be a distance between a first side 262 and a second side 264 of the first member. The width 916 of the second member may be a distance between a first side 266 and a second side 268 of the second member.

FIG. 7 is a schematic side view of the apparatus 200 in a configuration where the apparatus is attached to the part 204. The first side 262 of the first member 226 and the first side 266 of the second member can be seen. The first portion 258 of the base may have a lower extent, shown in dashed at 270, see also FIG. 6. The second portion 260 of the base may have an upper extent 272, see also FIG. 6. The upper extent 272 of the second portion of the base may be above the lower extent 270 of the first portion 258 of the base.

The first side 262 of the first member 226 may meet the part 204 along the first part surface 210 and the bevel surface 216 of the part when the apparatus 200 is attached to the part. The second side of the first member may meet the part along the first part surface and the bevel surface of the part in a similar manner. The first side 266 of the second member 228 and the second side 268 of the second member, not shown in FIG. 7, may meet the second part surface 212 when the apparatus is attached to the part. The low-friction pad 252 depicted in FIG. 5 may be disposed along the first contact element of the first member at every location where the first member meets the part, for example, between the first side 262 of the first member and the part. Similarly, the low-friction pad 254 may be disposed between the first side 266 of the second member and the part.

The first and second sides of the first and second members, along with the inner surface 240 of the base, best seen in FIG. 5, may form a seal with part 204. This seal may substantially prevent the flow of water or air into and out of an interior space between the housing and the part, excepting the intentional passages of water and air through the fluid conduit, the water supply assembly, and/or the water removal assembly.

Example 4

Figure 8:
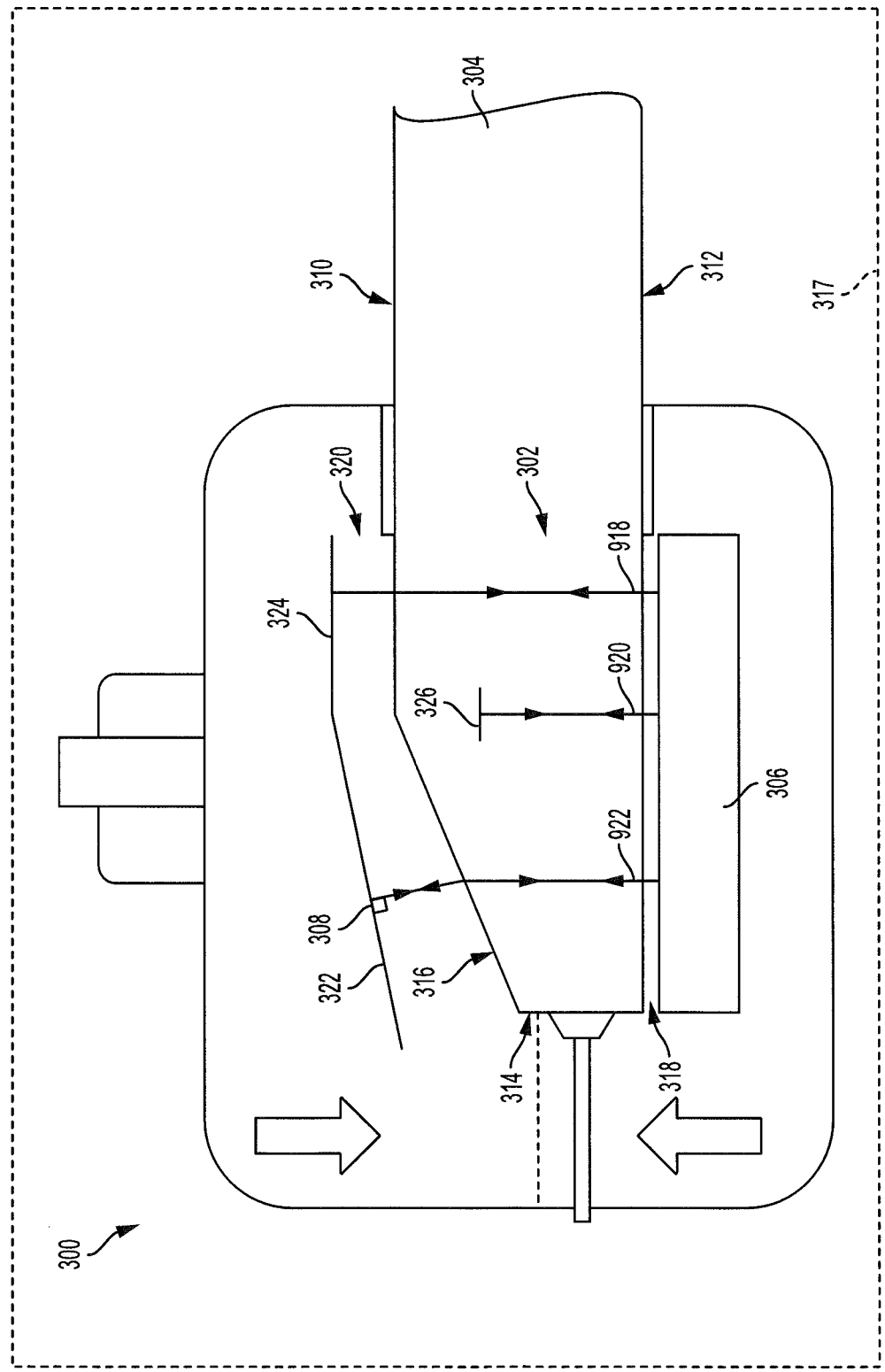
FIG. 8 is a schematic cross sectional view of another illustrative apparatus including a reflector plate, and an illustrative part.

This example describes another illustrative inspection apparatus for inspecting an end portion of a composite part, see FIG. 8.

FIG. 8 is a schematic cross sectional view of an embodiment of an illustrative apparatus, generally indicated at 300. Apparatus 300 may be used to inspect a composite end portion 302 of a part 304. Apparatus 300 may include an ultrasonic array 306 and a reflector plate 308.

Part 304 may be similar to any of the part 204 described in Example 3, the part 102 described in Example 2, or wing skin 14 described in Example 1. Part 304 may include a first part surface 310, a second part surface 312, a contact or end surface 314, and a bevel surface 316. These components of part 304 may be similar to the correspondingly numbered components of part 204.

Many of the components and features of apparatus 300 may be similar to inspection apparatus 200 described in Example 3. For example, apparatus 300 may include a housing having a base, a first member and a second member, a first contact element, a second contact element, and an inner surface of the base; a fluid conduit including first and second ends; low-friction pads, and a floating attachment junction. The first and second members may define a gap sized to receive the composite end portion. The base may include first and second portions formed with the first and second members, respectively. The first and second members may have first and second sides configured to meet the proximate surfaces of the part when the apparatus is attached to the part and the composite end portion is received within the gap. Apparatus 300 may be controlled and moved by a robotic arm connected to a controller assembly and coupled to the apparatus via a floating attachment junction. For further discussion of these components see Example 2.

Apparatus 300 may be configured to be used in an environment where the composite end portion 302 of the part 304 and at least a portion of apparatus 300 are both submerged in water. In this environment it may not be necessary to include a water supply assembly and a water removal assembly in apparatus 300. For example, apparatus 300 may be configured to inspect composite end portion 302 when submerged in a water tank 317.

Apparatus 300 may have a different internal configuration than apparatus 200 described above. Apparatus 300 may include an ultrasonic array 306 disposed proximate the end surface of the composite end portion of the part. Ultrasonic array 306 may be similar to ultrasonic array 208 or the array assembly 120 described above. Ultrasonic array 306 may be disposed proximate a portion of the second part surface 312 proximate the end surface of the part. The ultrasonic array may be spaced from the second part surface. A space 318 between the ultrasonic array and the part may be filled with water.

The apparatus 300 may include a reflector plate 308 proximate the bevel surface of the part. The reflector plate may be spaced from the bevel surface and oriented at an angle with respect to the bevel surface. A space 320 between the reflector plate and the bevel surface may be filled with water. Reflector plate 308 may be similar to reflector plate 150 described in Example 2. Reflector plate 308 may include an angled reflecting surface 322 and a parallel reflecting surface 324.

Apparatus 300 may be held in position with the part 304 in part by fluid conduit 326. The fluid conduit 326 may be similar to fluid conduit 122 and/or fluid conduit 236. Fluid conduit 326 may be configured to connect to a suction system configured to draw water from an interior space between the apparatus and the part. This suction force may impel the apparatus to make and maintain contact and alignment with the part when the part is received within the gap. In other words, the suction force may urge the part toward the apparatus.

To inspect part 304, the ultrasonic array 306 may emit ultrasonic sound waves into the part 304 and detect reflected ultrasonic sound waves that return to the ultrasonic array. For example, ultrasonic array may emit sound waves along representative rays 918, 920, and 922.

Ray 918 may be emitted by the ultrasonic array, travel through the water in the space 318 between the ultrasonic array and the second part surface 312 of the part 304, and enter the part through the second part surface. Ray 918 may then travel through the bulk of the part, exit the part through the first part surface 310, and enter the water filling the space 320 between the part and the reflector plate. Ray 918 may then encounter the parallel reflecting surface 324 of the reflector plate 308, which may be oriented parallel to the first part surface 310 of the part. If the ultrasonic array, the second part surface, the first part surface, and the parallel reflecting surface of the reflector plate are all oriented parallel to one another, then ray 918 may be reflected back along the path that ray 918 took from the ultrasonic array to the reflector plate. Thus, ray 918 may be reflected from the reflector plate back to the ultrasonic array where it may be detected.

Ray 920 may similarly be emitted by the ultrasonic array and enter the bulk of the part 304. Ray 920 may encounter a defect 326, such as a delamination. Defect 326 may be similar to delaminations 30 and 32 described in Example 1. Defect 326 may reflect ray 920 back to the ultrasonic array. Ray 920 may return along the same path it traveled between the array and the defect, it may be scattered to another portion of the array, it may be scattered away from array entirely, or it may be absorbed by the material of the part, among other possibilities.

Ray 922 may similarly be emitted by the ultrasonic array and enter the bulk of the part 304. Ray 922 may exit the part through the bevel surface 316 of the part and enter the water filling the space 320. The bevel surface may be oriented at a non-perpendicular angle to ray 922 which may cause ray 922 to bend as it exits the part. The angle through which ray 922 bends as it exits the part may depend upon the speed of ultrasonic sound waves in the part, the speed of ultrasonic sound waves in water, and the angle of the bevel surface with respect to ray 922. Ray 922 may then encounter the angled reflecting surface 322 of reflector plate 308 and be reflected back into the water filling the space 320. The angled reflecting surface of the reflector plate may be oriented at an angle with respect to the bevel surface so that ultrasonic sound waves travelling from the bevel surface to the reflector plate are reflected directly back to the bevel surface along the path from whence the waves came. That is, the angled portion of the reflector plate may be oriented perpendicularly to ray 922. In this case ray 922 will bend through the same angle as it enters the part and travel back to the ultrasonic array.

As with apparatus 200, the emitted and detected ultrasonic sound waves may be analyzed to determine a measurement of the quantity or density of defects in part 304 or to create an image or images of the interior of the part.

As the exterior views of apparatus 300 may be similar to the exterior views of apparatus 200, an end view and a side view are not shown.

Example 5

Figure 9:
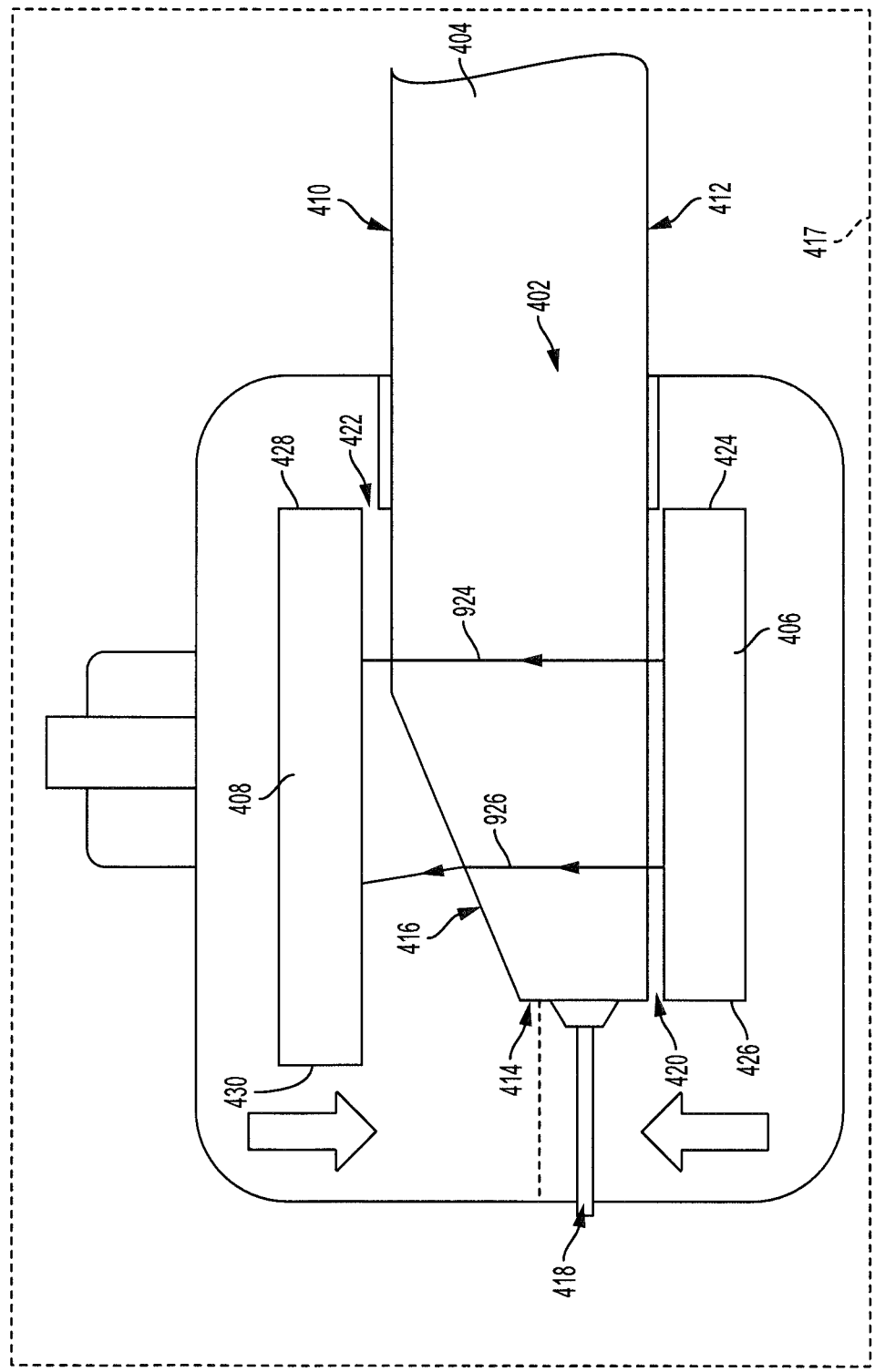
FIG. 9 is a schematic cross sectional view of another illustrative apparatus including two ultrasonic arrays, and an illustrative part.

This example describes another illustrative inspection apparatus for inspecting composite end portion of a part, see FIG. 9.

FIG. 9 is a schematic cross sectional view of an embodiment of an illustrative apparatus, generally indicated at 400. Apparatus 400 may be used to inspect a composite end portion 402 of a part 404. Apparatus 400 may include a first ultrasonic array 406 and a second ultrasonic array 408.

Part 404 may be similar to any of the part 304 described in Example 4, the part 204 described in Example 3, the part 102 described in Example 2, or wing skin 14 described in Example 1. Part 404 may include a first part surface 410, a second part surface 412, a contact or end surface 414, and a bevel surface 416. These components of part 404 may be similar to the correspondingly numbered components of part 204.

Many of the components and features of apparatus 400 are similar to inspection apparatus 200 described in Example 3. For example, apparatus 400 may include a housing including a base, a first member and a second member, a first contact element, a second contact element, and an inner surface of the base; fluid conduit including first and second ends; low-friction pads, and a floating attachment junction. The first and second members may define a gap sized to receive the composite end portion of the part. The base may include first and second portions formed with the first and second members, respectively. The first and second members may have first and second sides configured to meet the proximate surfaces of the part when the apparatus is attached to the part and the composite end portion is received within the gap. Apparatus 400 may be controlled and moved by a robotic arm connected to a controller assembly and coupled to the apparatus via a floating attachment junction. For further discussion of these components see Example 2.

Apparatus 400 may be configured to be used in an environment where the composite end portion 402 of the part 404 and at least a portion of apparatus 400 are both submerged in water. In this environment it may not be necessary to include a water supply assembly and a water removal assembly in apparatus 400. For example, apparatus 400 may be configured to inspect composite end portion 402 when submerged in a water tank 417.

Apparatus 400 may be held in position with the part 404 in part by a fluid conduit 418. The fluid conduit 418 may be similar to fluid conduit 122 and/or fluid conduit 236. Fluid conduit 418 may be configured to connect to a suction system configured to draw water from an interior space between the apparatus and the composite part. This suction force may impel the apparatus to make and maintain contact and alignment with the composite part.

Apparatus 400 may have a different internal configuration than apparatuses 300 and 200 described above. Apparatus 400 may include the first ultrasonic array 406, which may be disposed proximate the second part surface 412 of the composite part 404. Ultrasonic array 406 may be configured to only emit, only detect, or emit and detect ultrasonic sound waves. Apparatus 400 may include the second ultrasonic array 408, which may be disposed proximate the first part surface 410 of the part. Ultrasonic array 408 may be configured to only emit, only detect, or emit and detect ultrasonic sound waves. The ultrasonic arrays 406 and 408 may be similar to ultrasonic array 306, ultrasonic array 208, or the ultrasonic array assembly 120 described above. One or both of the ultrasonic arrays 406 and 408 may be spaced from the part 404. A space 420 between the first ultrasonic array and the part may be filled with water. A space 422 between the second ultrasonic array and the part may be filled with water.

To inspect part 404, the first ultrasonic array 406 may emit ultrasonic sound waves into or toward the part 404. The second ultrasonic array 408 may be configured to detect ultrasonic sound waves that have traveled through the part. The first ultrasonic array may also detect reflected ultrasonic sound waves that return to the first ultrasonic array. For example, the first ultrasonic array may emit sound waves along representative rays 924 and 926.

Ray 924 may be emitted by the first ultrasonic array 406, travel through the water in the space 420 between the first ultrasonic array and the second part surface 412 of the part 404, and enter the part through the second part surface. Ray 924 may then travel through the bulk of the part, exit the part through the first part surface 410, and enter the water filling the space 422 between the part and the second ultrasonic array 408. Ray 924 may then be detected by the second ultrasonic array. Alternately, if ray 924 encounters any defects in the part, the sound wave may be reflected back to and detected by the first ultrasonic array, much as ray 920 described in Example 4. In another alternative, if ray 924 encounters a defect in the part, the sound wave may be scattered away and not detected by either the first or second ultrasonic arrays.

Ray 926 may similarly be emitted by the first ultrasonic array 406 and enter the bulk of the part 404. Ray 926 may exit the part through the bevel surface 416 of the part and enter the water filling the space 422 between the part and the second ultrasonic array 408. The bevel surface may be oriented at a non-perpendicular angle to ray 926 which may cause ray 926 to bend as it exits the part. The angle through which ray 926 bends as it exits the part may depend upon the speed of ultrasonic sound waves in the part, the speed of ultrasonic sound waves in water, and the angle of the bevel surface with respect to ray 926. Ray 926 may then be detected by the second ultrasonic array 408.

The second ultrasonic array 408 may have an extended length relative to the first ultrasonic array 406. The first ultrasonic array may have a proximal end 424 and a distal end 426. The distal end 426 of the first ultrasonic array may be disposed proximate the contact surface 414 of the part. The second ultrasonic array may have a proximal end 428 and a distal end 430. The proximal ends of the first and second ultrasonic arrays may be disposed on opposite sides of the part, so that sound waves emitted from the proximal end 424 of the first ultrasonic array may travel straight through the composite part, as with ray 924, and be detected at the proximal end 428 of the second ultrasonic array. The distal end 430 of the second ultrasonic array may extend beyond the end surface 414 of the part. Since sound waves that exit the part through the bevel surface 416 may bend, as with ray 926, sound waves emitted from the distal end of the first ultrasonic array may be detected at the distal end of the second ultrasonic array.

As with apparatus 200, the emitted and detected ultrasonic sound waves may be analyzed to determine a measurement of the quantity or density of defects in part 404 or to create an image or images of the interior of the part.

As the exterior views of apparatus 400 may be similar to the exterior views of apparatus 200, an end view and a side view are not shown.

Example 6

Figure 10:
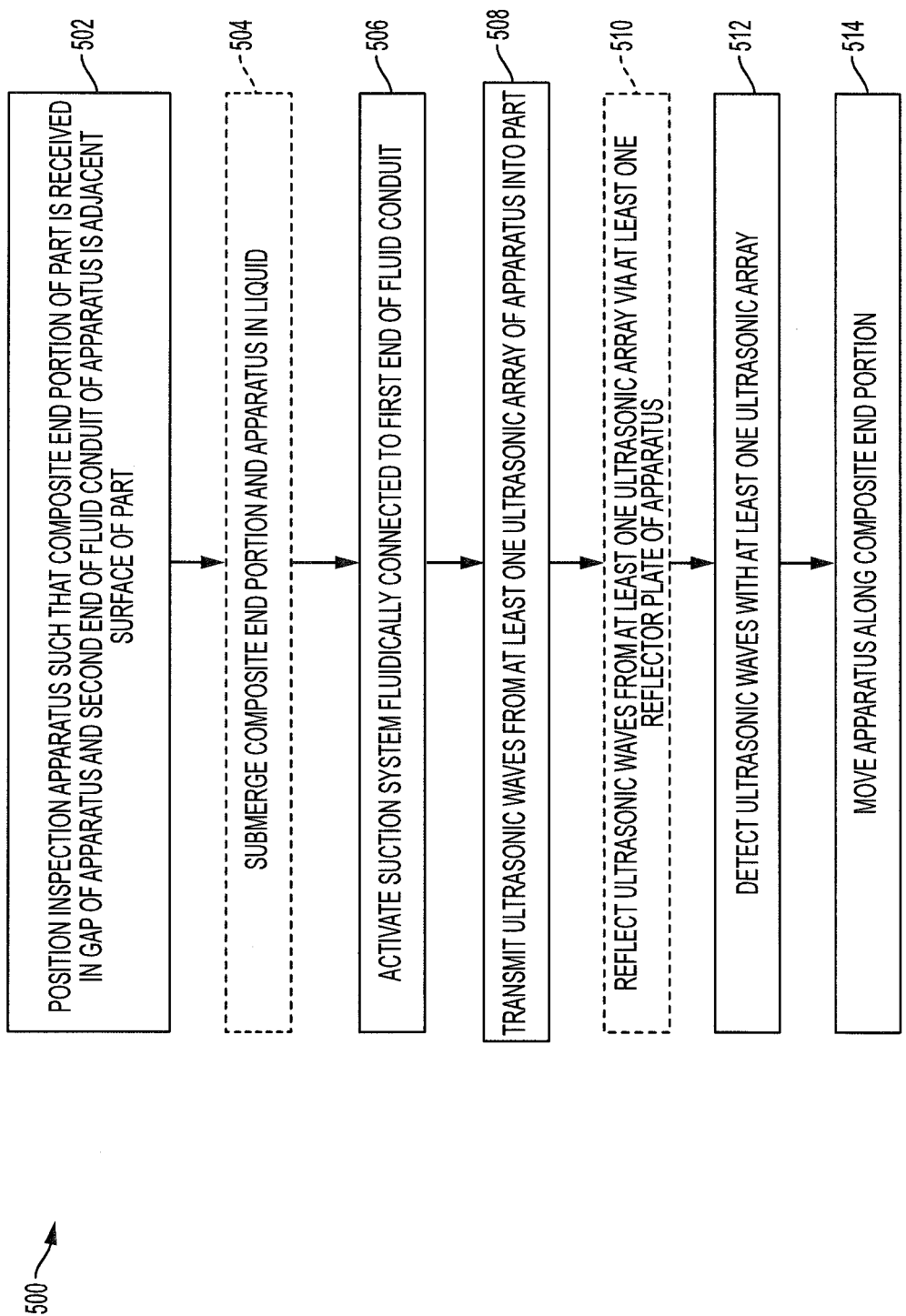
FIG. 10 is a flow chart illustrating a method of inspecting a composite end portion of a part.

This example describes an illustrative method of inspecting a composite end portion of a part, which may be used in conjunction with any of the apparatuses or systems described herein; see FIG. 10.

FIG. 10 depicts multiple steps of a method, generally indicated at 500 for inspecting a composite end portion of a part having a contact or end surface and opposed first and second part surfaces. The composite end portion may include a bevel surface. The contact surface may be perpendicular to the first and second surfaces. Method 500 may be used in conjunction with any of the inspection systems or apparatuses described in reference to FIGS. 4-9. Although various steps of method 500 are described and depicted in FIG. 10, the steps need not necessarily all be performed, and in some cases may be performed in a different order than the order shown.

Method 500 may include a step 502 of positioning an inspection apparatus such that the composite end portion of the part is received in a gap of the inspection apparatus and a second end of a fluid conduit of the apparatus is adjacent a surface of the part. By receiving the composite end portion in the gap, a first contact element of the inspection apparatus may contact the first part surface and a second contact element of the inspection apparatus may contact the second part surface. The surface of the part to which the second end of the fluid conduit is adjacent may be the contact surface, the bevel surface, or either of the first and second part surfaces.

The inspection apparatus may include a filler element having first and second filler surface. The first filler surface may be complementary to the bevel surface and the second filler surface may be co-planar with the first part surface when the composite end portion is received in the gap. When the composite end portion is received in the gap the first filler surface and the bevel surface of the part may form a first channel therebetween and the at least one ultrasonic array and the second filler surface may form a second channel therebetween. Method 500 may further comprise flowing fluid or liquid such as water through the first and second channels.

Method 500 may include a step 506 of activating a suction system fluidly or fluidly connected to a first end of the fluid conduit. Activating the suction system may draw the contact surface of the part toward the second end of the fluid conduit of the inspection apparatus. By receiving the composite end portion within the gap of the inspection apparatus in step 502, and drawing the contact surface of the part toward the apparatus in step 506, the apparatus may be self-aligned and in proper position for inspecting the composite end portion. The suction system, together with the fluid conduit, may be configured to suction air or water, so that the inspection apparatus may be used in an air environment or in a water environment.

Method 500 may include a step 508 of transmitting ultrasonic waves from at least one ultrasonic array of the inspection apparatus into the part. The at least one ultrasonic array may be a linear array or a phased linear array. The ultrasonic sound waves may travel through the part and may be scattered, reflected, or absorbed by any defects present in the part or on the surface of the part. The ultrasonic sound waves may be emitted continuously or in bursts or pulses. The emitted sound waves may travel into the composite end portion of the part and/or untrimmed portions of the part proximate the composite end portion. In the case where the inspection apparatus includes a filler element, transmitting ultrasonic waves may include transmitting ultrasonic waves from the at least one ultrasonic array through the filler element and into the part. The ultrasonic waves may be transmitted via a first ultrasonic array of the at least one ultrasonic array.

Method 500 may include a step 512 of detecting ultrasonic waves with the at least one ultrasonic array. The detected sound waves may have passed through the part and been reflected by a reflective surface, may have reflected off a surface of the part itself, or may have been reflected or scattered by a defect in the part. By analyzing the detected ultrasonic sound waves, and perhaps comparing to the emitted sound waves, the composite end portion of the part may be inspected for defects. The detected sound waves may be used to generate an image or images of the composite end portion of the part, and/or an image or images of the part proximate the composite end portion. The ultrasonic waves may be detected via a second ultrasonic array of the at least one ultrasonic array.

Method 500 may include a step 514 of moving the inspection apparatus along the composite end portion. Step 514 may be performed at substantially the same time as steps 508 and 512. That is, the at least one ultrasonic array may be transmitting sound waves into the part and detecting sound waves from the part as the at least one array is moved along the composite end portion of the part. Thus, a scan of the composite end portion of the part may be performed. Moving the ultrasonic array along the composite end portion may include moving the ultrasonic array via a robotic arm. Alternately, the ultrasonic array may be moved by hand.

Method 500 may optionally include a step 504 of submerging the composite end portion of the part and the inspection apparatus in liquid, such as water. Submerging the composite end portion and the apparatus in liquid may facilitate coupling of sound waves into and out of the composite end portion of the part. These components may be submerged in a water tank or other container.

Method 500 may optionally include a step 510 of reflecting ultrasonic sound waves from the at least one ultrasonic array via at least one reflector plate of the inspection apparatus. The reflected ultrasonic sound waves may have been transmitted by the at least one ultrasonic array. The ultrasonic sound wave may be reflected off of one or more than one reflecting surface of the at least one reflector plate.

Example 7

This example describes an illustrative system for inspecting an edge of a composite part. The illustrative system may include a reflector assembly, see FIG. 11.

Figure 11:
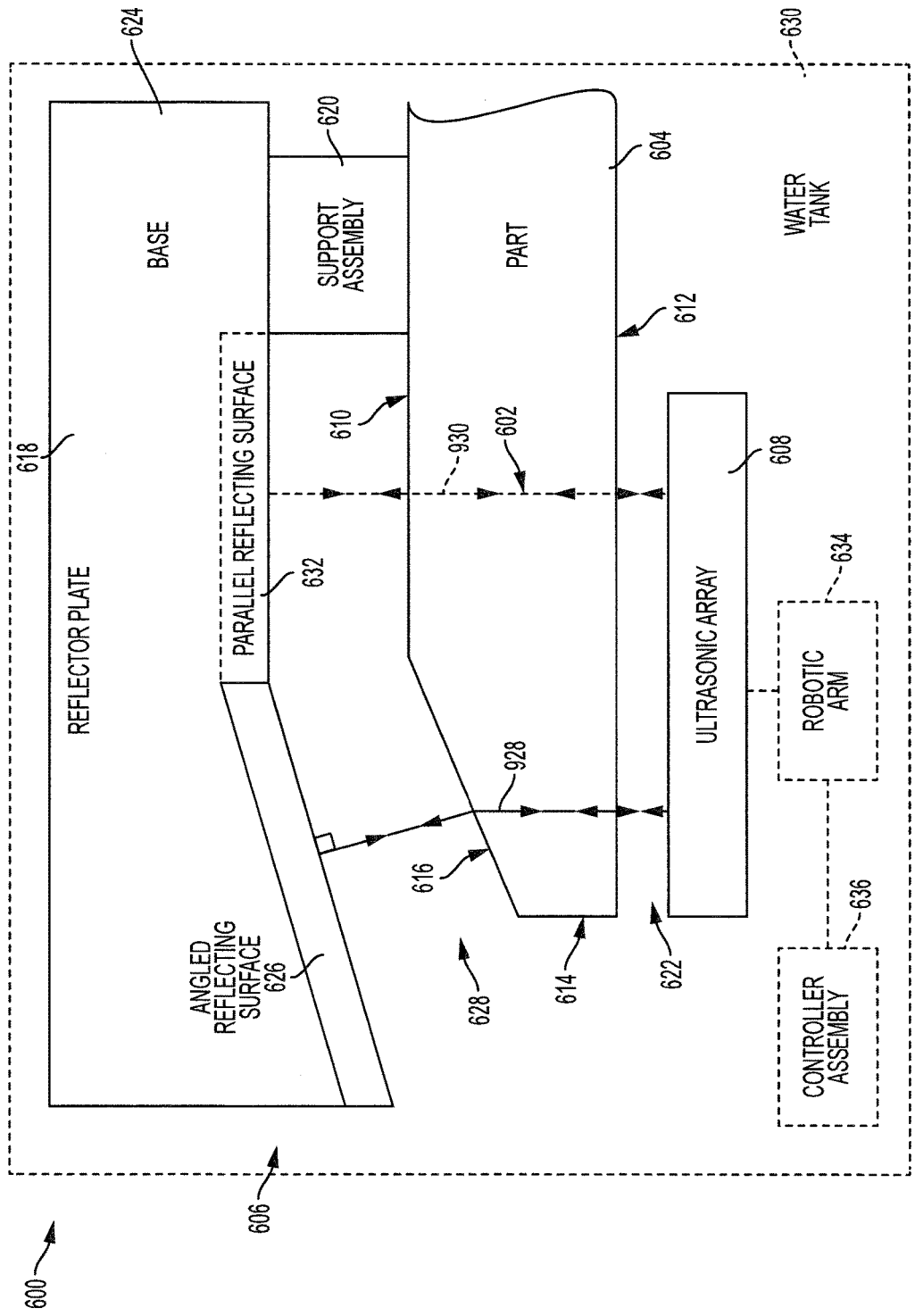
FIG. 11 is a block diagram of another illustrative system, including an illustrative reflector assembly and an illustrative part.

FIG. 11 is a block diagram of an illustrative inspection system, generally indicated at 600. Inspection system 600 may be used to inspect a composite end portion 602 of a part 604. System 600 may include a reflector assembly, generally indicated at 606, and an ultrasonic array 608.

Part 604 may be similar to composite part 102 described in Example 2. The composite end portion 602 may have a first part surface 610 and a second part surface 612, which may be opposed to each other. The composite end portion may have a contact or end surface 614 and a bevel surface 616. The end surface 614 may be perpendicular to the first and second part surfaces 610 and 612.

Reflector assembly 606 may include a reflector plate 618 and a support assembly 620. Inspection system 600 may operate under similar principles as apparatus 300 described in Example 4. However, where the reflector plate 308 of apparatus 300 may be carried by the housing of apparatus 300, reflector plate 618 may be stationary relative to the part 604 as the part is inspected.

Ultrasonic array 608 may be similar to any of the ultrasonic array or array assemblies described herein. The ultrasonic array may be placed adjacent to, but spaced from the first part surface 610 during inspection of the part 604. That is, there may be a space 622 between the ultrasonic array and the first part surface of the part.

The reflector plate 618 may have a base 624 and an angled reflecting surface 626. The support assembly 620 may be attached to the base and may be configured to support the reflector plate 618 on the first part surface 610 of the part. When so supported by the part the base 624 and the angled reflecting surface 626 may be adjacent to, but spaced from the first part surface 610 and the bevel surface 616 of the part, respectively. That is, when the reflector plate is operatively coupled to the part via the support assembly 620, there may be a space 628 between the reflector plate and the part. The support assembly may consist of a set of posts disposed along the base 624 of the reflector plate, or a single support member extending along the base of the reflector plate. The support assembly may include mechanisms to removably couple the support assembly to the part without damaging the part, for example one or more suction cups. Alternately, the support assembly may couple to the part via a vacuum system such as the fluid conduit 122 and the associated suction system 136 described in Example 2. Any appropriate means may be used to attach the support assembly to the part.

In an illustrative example, the composite end portion 602 of the part 604 may be the edge 18 of a wing skin 14 proximate an access hole 16, as described in Example 1. That is, the composite end portion may form a first closed loop. In this case, the reflector plate may form a second closed loop sized so as to be disposed adjacent the edge 18 of the hole 16 when the reflector plate 618 is supported by the support assembly 620 on the first part surface 610 of the part.

Inspection system 600 may be configured to inspect part 604 in an environment where the reflector assembly 606, the composite end portion 602, and the ultrasonic array 608 are submerged in water. For example, the reflector assembly, the composite end portion, and the ultrasonic array may be submerged in a water tank 630.

The angled reflecting surface 626 may be angled to be perpendicular to ultrasonic sound waves transmitted from the ultrasonic array 608 and through the bevel surface 616. For example, the ultrasonic array 608 may emit an ultrasonic sound wave travelling along an exemplary ray 928. Ray 928 may have a similar path as ray 922 described in reference to FIG. 8. If the angled reflecting surface 626 is angled perpendicularly to the ray 928, then this ray may travel back through the part to the ultrasonic array along the same path as ray 928 took from the array to the reflector plate 618. The angled reflecting surface may be angled according to the speed of ultrasonic sound waves in the part, the speed of ultrasonic sound waves in water, and a bevel angle of the bevel surface 616 with respect to the first part surface 610.

The base 624 of the reflector plate 618 may include a parallel reflecting surface 632. Parallel reflecting surface 632 may be oriented perpendicularly to ultrasonic sound waves transmitted from the ultrasonic array 608 and through the first part surface 610 of the part 604. The parallel reflecting surface may be parallel to the first part surface. For example, the ultrasonic array may emit an ultrasonic sound wave travelling along an exemplary ray 930. Ray 930 may have a similar path as ray 918 described in reference to FIG. 8. If the ultrasonic array, the first part surface 610, the second part surface 612 and the parallel reflecting surface of the base are all aligned parallel to one another, then ray 930 may travel from the ultrasonic array, through the part, reflect directly back off the parallel reflecting surface, travel back through the part, and be detected by the ultrasonic array proximate where ray 930 was emitted.

Inspection system 600 may include a robotic arm 634 and a controller assembly 636. Robotic arm 634 may be similar to robotic arm 106 described in reference to FIG. 4. The robotic arm may be coupled to the ultrasonic array and move the array along the composite end portion 602. In such a case the robotic arm may be controlled by the controller assembly, which may be similar to controller assembly 108. Alternately, the ultrasonic array may be moved along the composite end portion by hand or some other mechanism.

As in the other examples described herein, the inspection system 600 may provide a quantitative or qualitative account of the defects in the part 604 by analyzing the emitted and detected ultrasonic sound waves.

Example 8

This example describes an illustrative system, generally indicated at 700, for inspecting a composite end portion of a part. The illustrative system may include a reflector assembly, see FIGS. 12-13.

Figure 12:
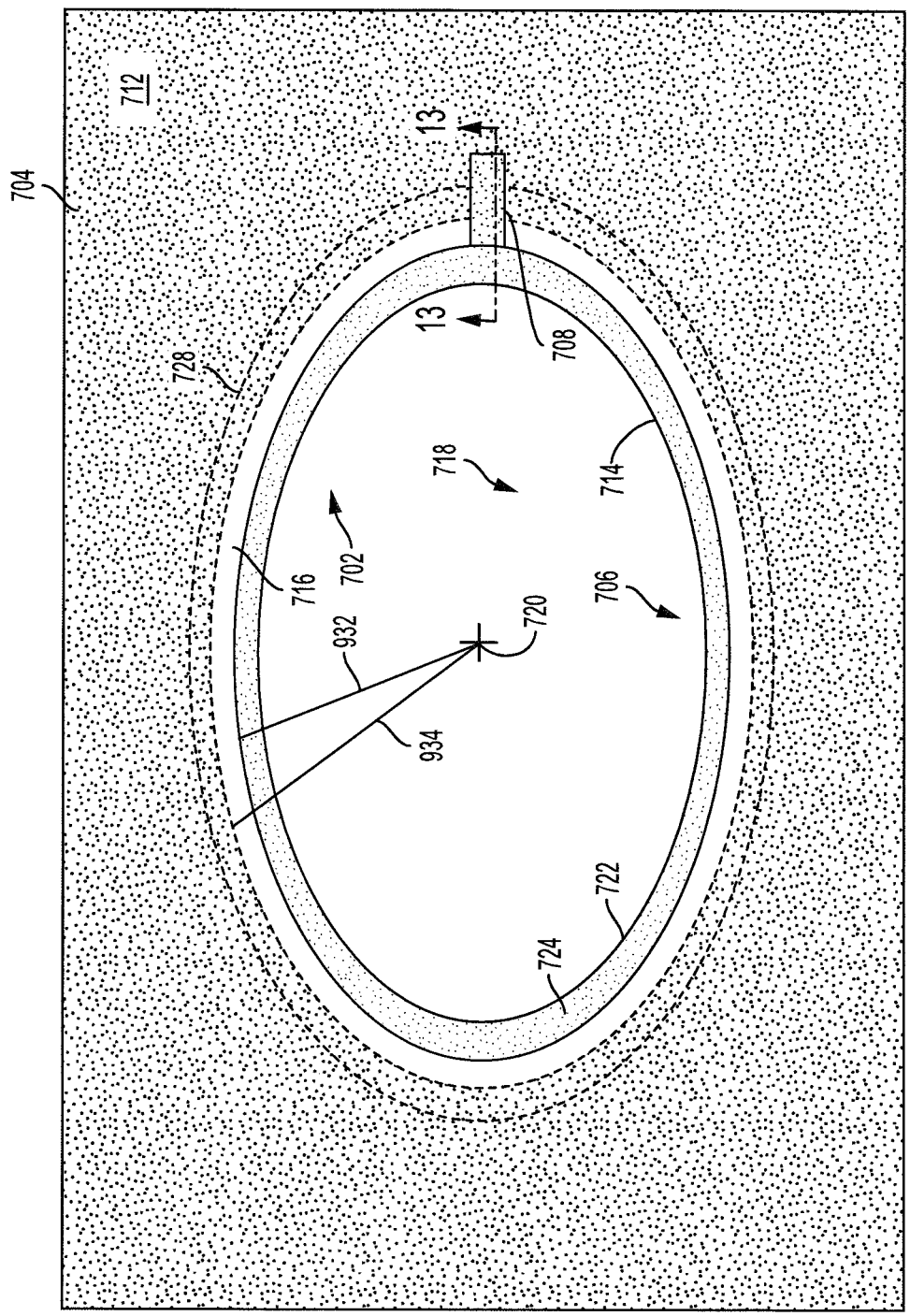
FIG. 12 is a schematic view of the wing access hole of FIG. 1, as viewed from inside the hole, showing an illustrative system, including an illustrative reflector plate and an ultrasonic array.

FIG. 12 is a schematic view of a composite end portion 702 of a wing skin 704, as viewed from inside the wing skin. The inspection system 700 may include a reflector assembly 706 and an ultrasonic array 708.

Figure 13:
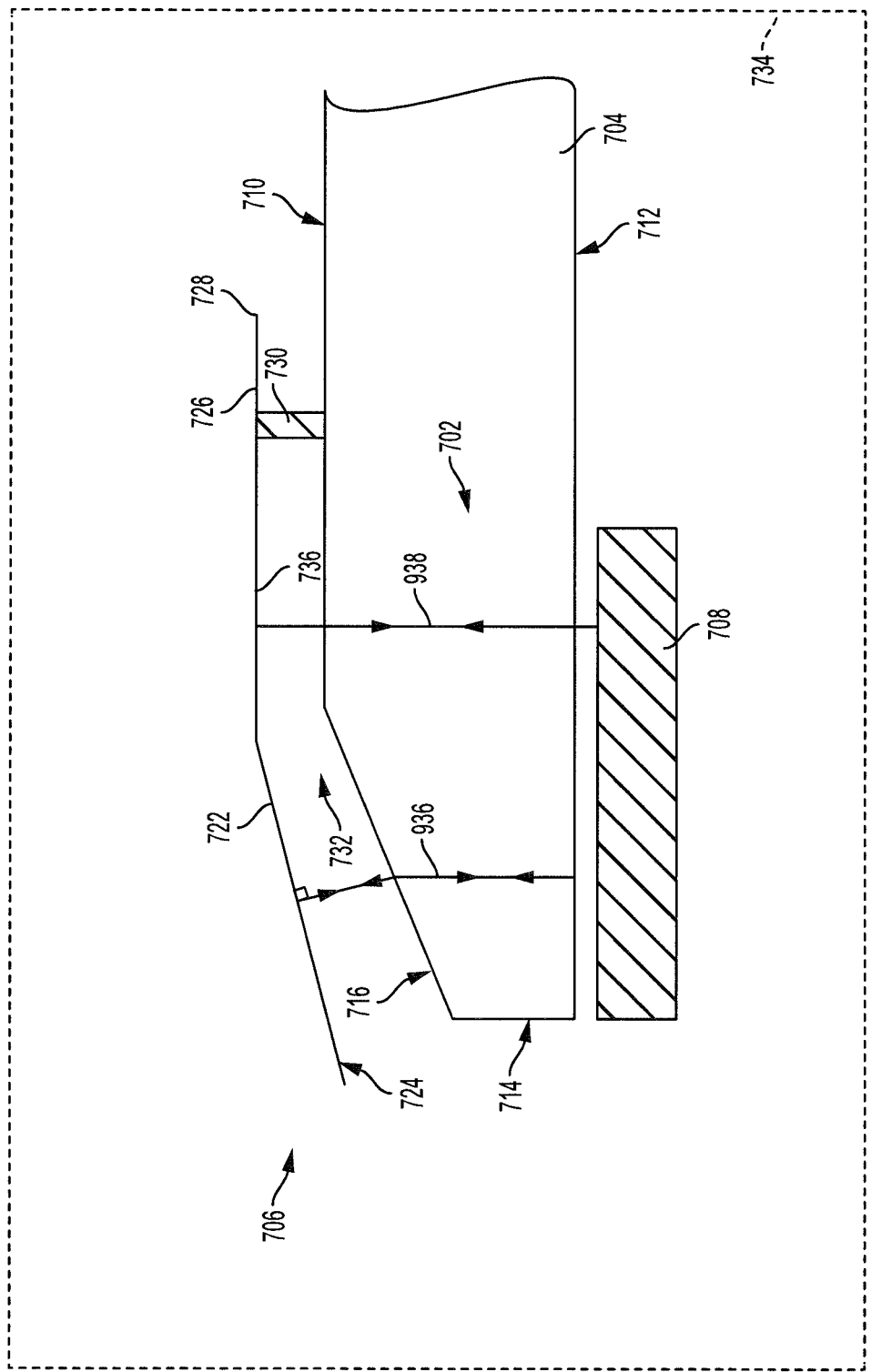
FIG. 13 is a schematic cross-sectional view of the system of FIG. 12, taken at 13-13 in FIG. 12.

The wing skin 704 may have a second part surface 712 which may be an interior surface of a wing, a first part surface 710, best seen in FIG. 13, which may be an exterior surface of a wing, a contact or end surface 714, and a bevel surface 716. The end surface 714 may substantially define an access hole 718, which may be similar to access hole 16 described in reference to FIG. 2. The bevel surface 716 may extend from an inner distance 932 proximate the end surface 714 to an outer distance 934, shown in dashed as the bevel surface may be on an exterior side of the wing skin. Distances 932 and 934 may be measured from a center 720 of the access hole.

The reflector assembly 706 may include a reflector plate 722. The reflector plate may be sized and configured to be proximate the end portion 702 when the reflector assembly 706 is operatively coupled to the wing skin 704. The reflector assembly may be coupled to the wing skin on the first part surface 710 of the wing skin. The reflector plate may include an angled reflecting surface 724, a portion of which may be viewable from a vantage point within the wing as is shown in FIG. 12. The reflector plate may have a base 726, best seen in FIG. 13, the base having an outermost end 728 shown in dashed lines as the outermost end of the base may not be viewable from within the wing.

Ultrasonic array 708 may be similar to ultrasonic array 608 described in reference to FIG. 11. The ultrasonic array may be held in position proximate the end portion 702 of the wing skin by a robotic arm, see for example in FIG. 11. Such a robotic arm may move the ultrasonic array 708 along the composite end portion.

FIG. 13 is a schematic cross-sectional view, taken at 13-13 in FIG. 12, of the reflector assembly 706, the composite end portion 702 of the wing skin 704, and the ultrasonic array 708.

The reflector assembly 706 may include a support assembly 730. The support assembly may be attached to the base 726 and may be configured to support the reflector plate 722 on the first part surface 710 of the wing skin 704. When supported, the base and the angled reflecting surface 724 may be adjacent to, but spaced from, the first part surface and the bevel surface 716 of the wing skin, respectively. A space 732 between the wing skin and the reflector assembly may be filled with water, as the reflector assembly, the composite end portion, and the ultrasonic array may be submerged in water, for example in a water tank 734. The support assembly 730 may include a set of posts distributed along the reflector assembly, or a single spacing member distributed along the reflector assembly, among others.

The angled reflecting surface 724 may be angled to be perpendicular to ultrasonic sound waves transmitted from the ultrasonic array 708 and through the bevel surface 716. For example, the ultrasonic array may emit sound waves that travel along ray 936, which may be similar to ray 928 described in Example 7, or to ray 922 described in Example 4.

Reflector plate 722 may also include a parallel reflecting surface 736 which may be similar to reflecting surface 632 described in Example 7. Sound waves, for example along a ray 938, may travel from the ultrasonic array, through the wing skin 704, reflect off the parallel reflecting surface and return to the ultrasonic array. Ray 938 may be substantially similar to ray 930 described in Example 7 and/or ray 918 described in Example 4.

Example 9

Figure 14:
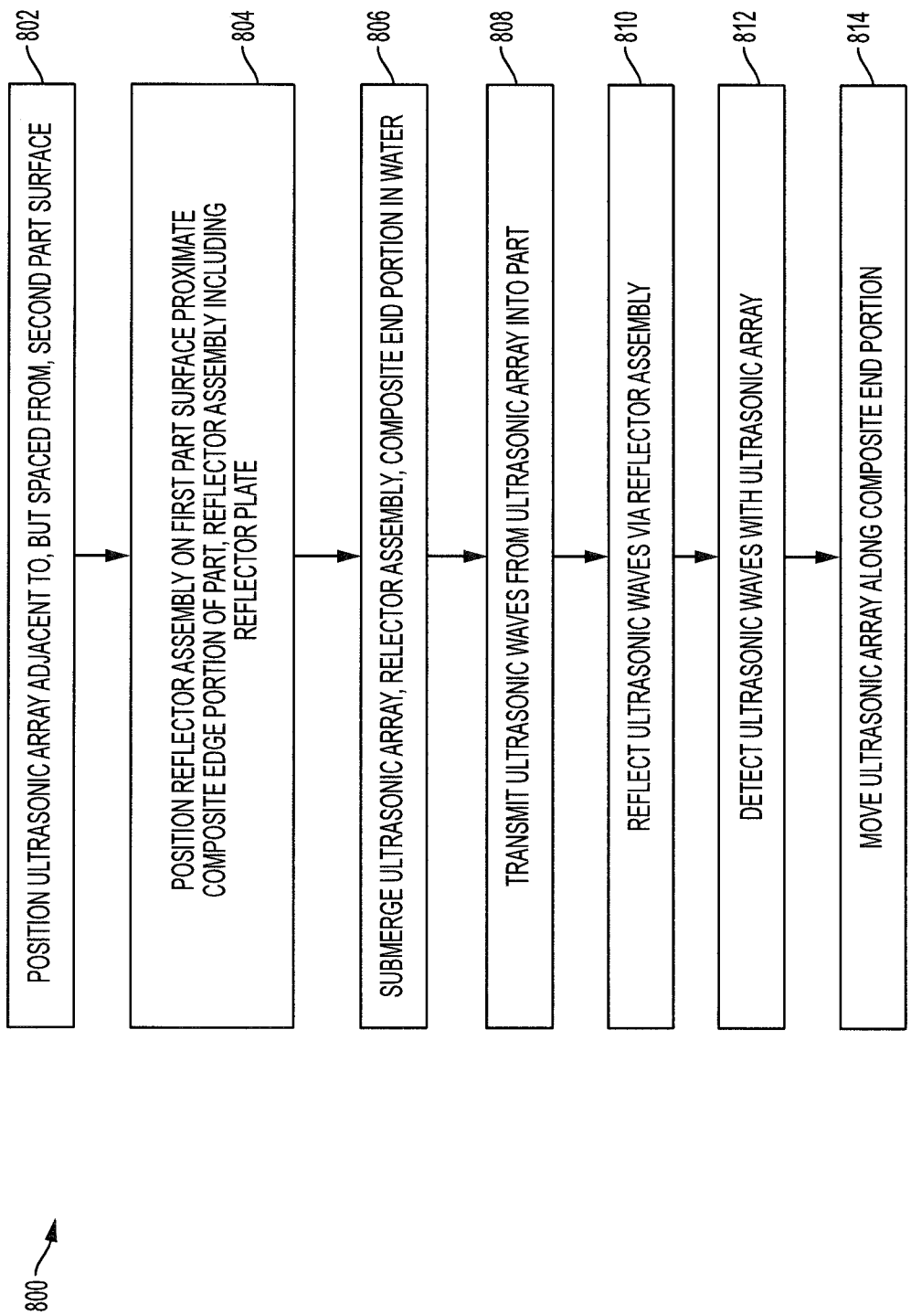
FIG. 14 is a flow chart illustrating a method of inspecting a composite end portion of a part.

This example describes an illustrative method of inspecting a composite end portion of a part, which may be used in conjunction with any of the apparatuses or systems described herein; see FIG. 14.

FIG. 14 depicts multiple steps of a method, generally indicated at 800 for inspecting a composite end portion of a part having a contact or end surface, opposed first and second part surfaces, and a bevel surface. The end surface may be perpendicular to the first and second surfaces. Method 800 may be used in conjunction with any of the inspection systems or apparatuses described in reference to FIGS. 11-13. Although various steps of method 800 are described and depicted in FIG. 14, the steps need not necessarily all be performed, and in some cases may be performed in a different order than the order shown.

Method 800 may include a step 802 of positioning an ultrasonic array adjacent to, but spaced from, the second part surface of the composite part. Spacing the ultrasonic array from the second part surface of the part may permit water to be disposed between the ultrasonic array and the part. Having water between the array and the part may facilitate the coupling of ultrasonic sound waves between the array and the part.

Method 800 may include a step 804 of positioning a reflector assembly on the first part surface adjacent to or proximate the composite end portion of the part, the reflector assembly including a reflector plate and a support assembly. The reflector assembly may be reflector assembly 606 or 706 described above. The reflector plate may have a base and an angled reflecting surface. The angled reflecting surface may be angled to be perpendicular to ultrasonic sound waves transmitted from the ultrasonic array and through the bevel surface.

The support assembly may be attached to the base and may be configured to support the reflector plate on the second surface of the part. Thus supported, the base and the angled reflecting surface may be adjacent to, but spaced from, the second surface and the bevel surface of the part, respectively. Supporting the reflector plate at a position spaced form the composite part may permit water to be disposed between the reflector plate and the part. Water may facilitate coupling of sound waves into and out of the composite part.

Method 800 may include a step 806 of submerging the ultrasonic array, the reflector assembly, and the composite end portion of the part in liquid, such as water. These components may be submerged in a water tank or other container. Such a water environment may allow ultrasonic sound waves to enter and exit the composite part easier than in a similar air environment.

Method 800 may include a step 808 of emitting or transmitting ultrasonic sound waves from the ultrasonic array into the part. The ultrasonic array may be a linear array or a phased linear array. The ultrasonic sound waves may travel through the part and may be scattered, reflected, or absorbed by any defects present in the part or on the surface of the part. The ultrasonic sound waves may be emitted continuously or in bursts or pulses. The emitted sound waves may travel into the composite end portion of the part and/or untrimmed portions of the part proximate the composite end portion.

Method 800 may include a step 810 of reflecting ultrasonic waves via the reflector assembly. The reflected ultrasonic waves may be those ultrasonic waves transmitted from the ultrasonic array. The ultrasonic waves may be reflected off of one reflecting surface or more than one reflecting surface of the reflector assembly. For example, the waves may be reflected off an angled reflecting surface and a parallel reflecting surface as described in reference to FIG. 11 or 13.

Method 800 may include a step 812 of detecting ultrasonic sound waves with the ultrasonic array. The detected sound waves may have passed through the part and been reflected by the reflector assembly or may have been reflected or scattered by a defect in the part. By analyzing the detected ultrasonic sound waves, and perhaps comparing to the emitted sound waves, the composite end portion of the part may be inspected for defects. The detected sound waves may be used to generate an image or images of the composite end portion of the part, and/or an image or images of the part proximate the composite end portion.

Method 800 may include a step 814 of moving the ultrasonic array along the composite end portion of the part. Step 814 may be performed at substantially the same time as steps 808 and 812. That is, the ultrasonic array may be transmitting sound waves into the part and detecting sound waves from the part as the array is moved along the composite end portion of the part. Thus, a scan of the composite end portion of the part may be performed. Moving the ultrasonic array along the composite end portion may include moving the ultrasonic array via a robotic arm. Alternately, the ultrasonic array may be moved by hand.

Example 10

This example describes three illustrative embodiments of coupler assemblies, see FIGS. 15-20. Each of the three illustrative embodiments may be part of or used with any of the systems, methods, or apparatuses described herein.

Figure 15:
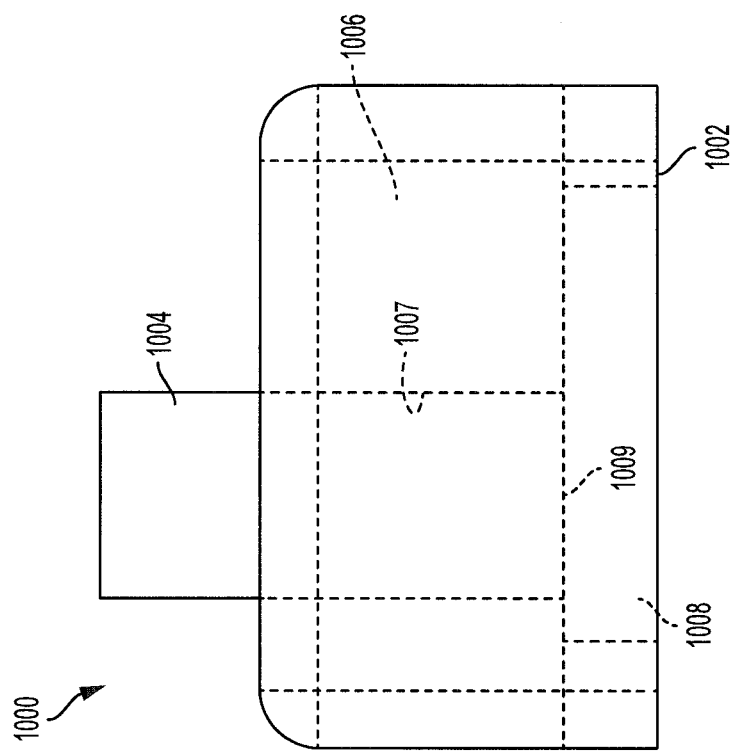
FIG. 15 is a schematic side view of an illustrative coupler assembly of the apparatus of FIG. 4.

FIG. 15 is a schematic side view of an illustrative coupler assembly, generally indicated at 1000. Coupler assembly 1000 may include a first coupler 1002 attached to one of the first and second members of an inspection apparatus, a second coupler 1004 movably attached to the first coupler, and at least one bias element, for example, bias element 1006.

First coupler 1002 may be attached to the inspection apparatus by any appropriate means. The first coupler may be rigidly attached to the inspection apparatus, so that the first coupler and the inspection apparatus move through three dimensional space together. First coupler 1002 may form a casing or housing for one or more other components of the coupler assembly 1000. In some examples, the first coupler may include a top wall (not shown) configured to cover one or more other components of the coupler assembly.

Second coupler 1004 may be configured to be attached to (or coupled with) a robotic arm, see FIGS. 4 and 11. Second coupler 1004 may be configured to move relative to the first coupler along at least two axes (or at least three axes). Second coupler 1004 may be a rod, a post, a shaft, or any other appropriate member and may have a nominal or equilibrium position within coupler assembly 1000.

Bias element 1006 may be configured to urge the second coupler 1004 toward the nominal position, such as when the second coupler is moved away from the nominal position (and/or relative to the first coupler). For example, bias element 1006 may be a flexible and compressible rubber ring surrounding the second coupler 1004. The rubber ring may include a hole or aperture 1007 and the second coupler 1004 may be partially received within the hole.

If the second coupler is displaced or moved from the nominal position thereby compressing the rubber ring, then this compression may provide a net force urging the second coupler back to the nominal position. In the case where the bias element 1006 surrounds the second coupler 1004 in two directions the second coupler may move relative to the first coupler 1002 along two axes. In the view of FIG. 15, second coupler 1004 is shown displaced to the left relative to the first coupler 1002. In this case bias element 1006 would allow for this leftward displacement and urge the second coupler back toward the nominal position, that is, to the right in FIG. 15.

Coupler assembly 1000 may include a second bias element 1008. Second bias element may allow the second coupler 1004 to move relative to the first coupler 1002 along a third axis, namely up and down in the view of FIG. 15. The second bias element may be a flexible and compressible rubber disc or pad. The second coupler 1004 may have an end portion 1009 that is received within the hole 1007. The rubber pad 1008 may be attached to the end portion 1009.

Figure 16:
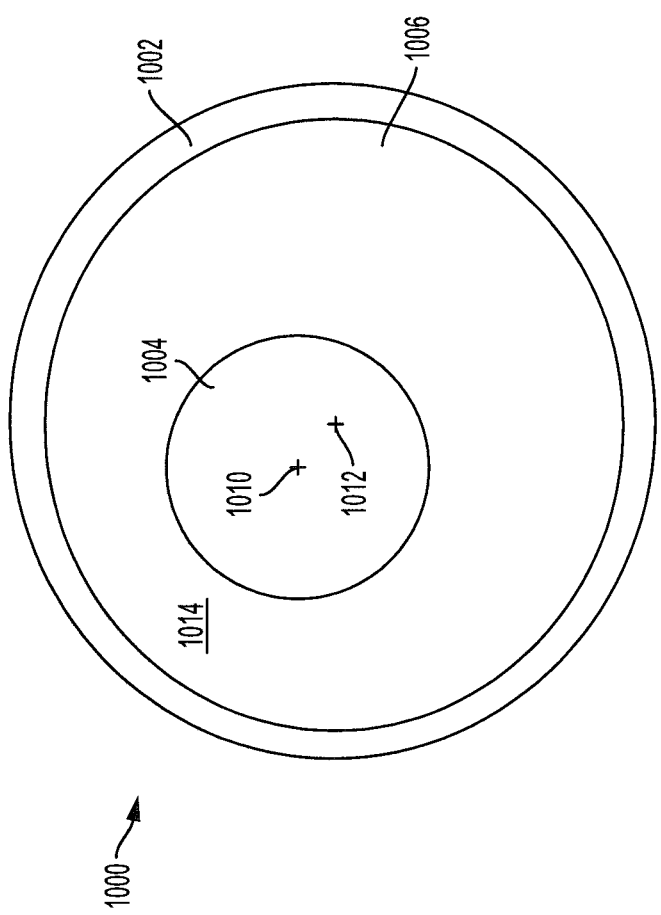
FIG. 16 is a schematic top view of the illustrative coupler assembly of FIG. 15.

FIG. 16 is a schematic top view of illustrative coupler assembly 1000. In the view of FIG. 16, a center 1010 of the second coupler 1004 has been displaced from a nominal or equilibrium position of a center 1012 of the coupler assembly 1000. The bias element 1006 may be compressed in a region 1014 between the second coupler 1004 and the first coupler 1002. This compression may deliver a force to the second coupler urging the center 1010 of the second coupler back to the center 1012 of the coupler assembly. In some examples, the first coupler may include a top wall (not shown) configured to cover one or more other components of the coupler assembly.

Figure 17:
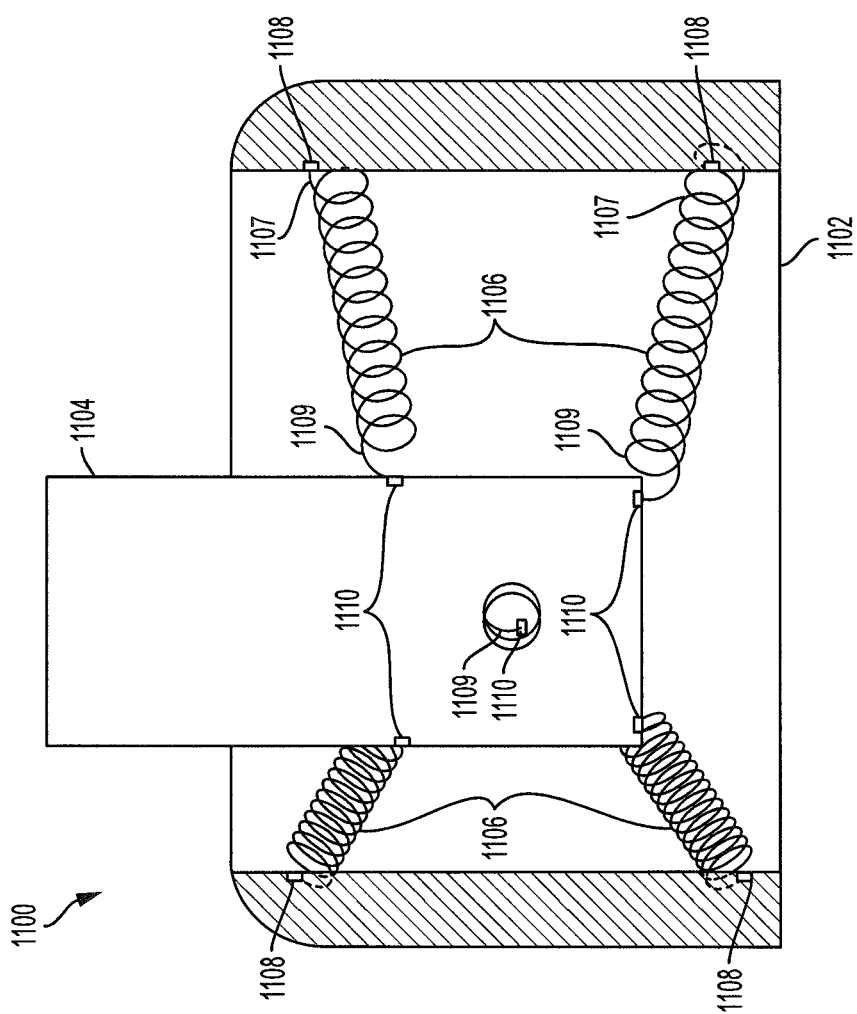
FIG. 17 is a schematic cross-sectional view of another illustrative coupler assembly of the apparatus of FIG. 4, taken at 17-17 in FIG. 18.

FIG. 17 is a schematic cross sectional side view of another illustrative coupler assembly, generally indicated at 1100. Coupler assembly 1100 may include a first coupler 1102 attached to one of the first and second members of an inspection apparatus, a second coupler 1104 movably attached to the first coupler, and one or more bias elements 1106.

First coupler 1102 may be attached to the inspection apparatus by any appropriate means. The first coupler may be rigidly attached to the inspection apparatus, so that the first coupler and the inspection apparatus move through three dimensional space together. First coupler 1102 may form a casing or housing for one or more other components of the coupler assembly 1100.

Second coupler 1104 may be configured to be attached to a robotic arm, see FIGS. 4 and 11. Second coupler 1104 may be configured to move relative to the first coupler along at least two axes (or at least three axes). Second coupler 1104 may be a rod, a post, a shaft, or any other appropriate member and may have a nominal or equilibrium position within coupler assembly 1100.

Bias element(s) 1106 may be configured to urge the second coupler 1104 toward the nominal position, such as when the second coupler is moved away from the nominal position (and/or relative to the first coupler). For example, bias elements 1106 may be at least one spring 1106. If the second coupler is displaced or moved from the nominal position thereby compressing the one or more of the springs, then this compression may provide a net force urging the second coupler back to the nominal position. The spring(s) 1106 may be disposed around the second coupler 1104 in two or three dimensions. Thus, the second coupler may be configured to move relative to the first coupler 1102 along at least two axes (or at least three axes). In the view of FIG. 17, second coupler 1104 is shown displaced to the left relative to the first coupler 1102. In this case bias elements 1106 would allow for this leftward displacement and urge the second coupler back toward the nominal position, that is, to the right of FIG. 17.

In another case, if the second coupler 1104 were displaced in a vertical direction in the view of FIG. 17, then the springs 1106 may be oriented so that the subsequent compression and extension of the springs results in a net force in the opposite vertical direction as the displacement. While six springs are depicted in FIG. 18, any number of springs may be appropriate and the springs may be distributed around the second coupler in any appropriate fashion.

The springs 1106 may be coupled to the first and second couplers 1102 and 1104 by any appropriate means. For example, the springs may have a first end portion 1107 configured to be attached to the first coupler via base connectors 1108, such as bolts, screws, rivets, etc. and/or the like. In some example, base connectors 1108 may be openings, slots, or apertures sized to receive the first end portions of springs 1106. The springs may have a second end portion 1109 configured to be attached to the second coupler via rod attachment connectors 1110, such as bolts, screws, rivets, etc. and/or the like. In some example, rod connectors 1110 may be openings, slots, or apertures sized to receive the second end portions of springs 1106. For any particular spring, the base connector and the rod connector may be disposed with at any relative vertical separation. That is, the base connectors 1108 may be at the same vertical location as the rod connectors 1110, relative to the view of FIG. 17, or at different vertical locations.

Figure 18:
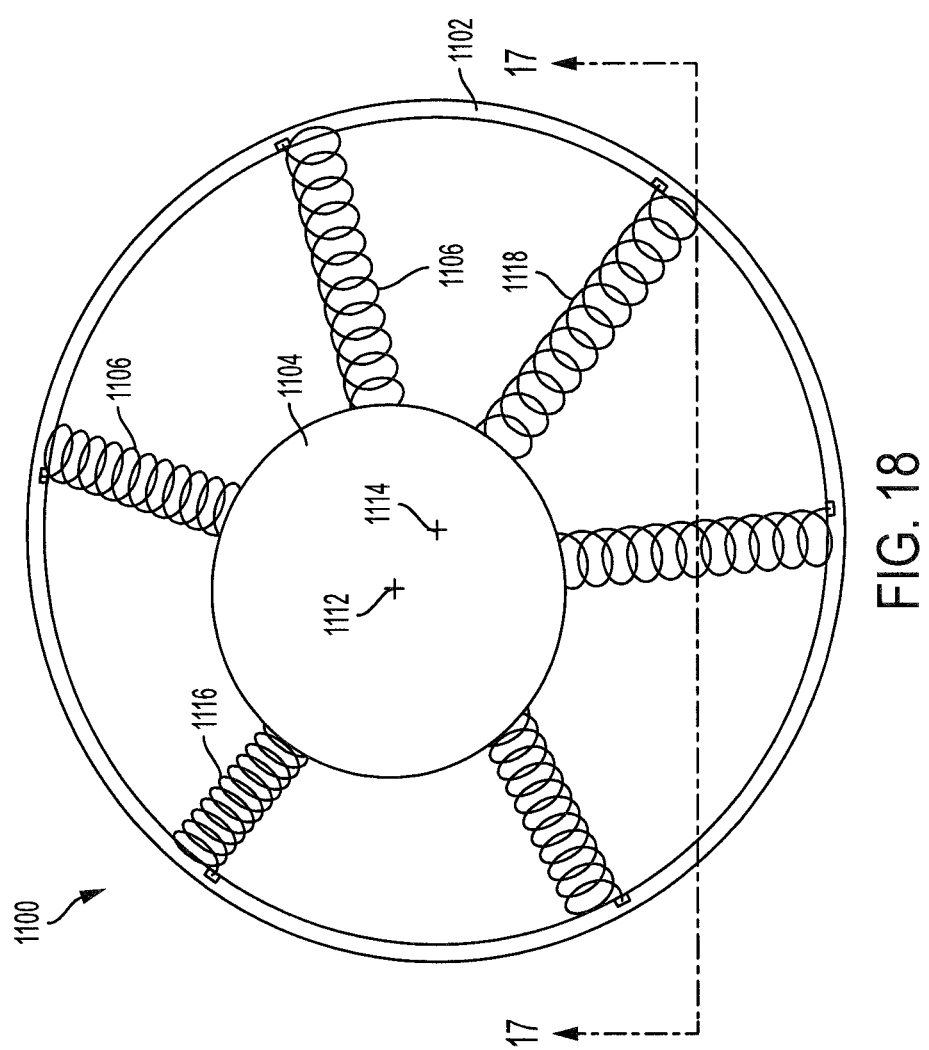
FIG. 18 is a schematic top view of the illustrative coupler assembly of FIG. 17.

FIG. 18 is a schematic top view of illustrative coupler assembly 1100. In the view of FIG. 18, a center 1112 of the second coupler 1104 has been displaced from a nominal or equilibrium position of a center 1114 of the coupler assembly 1100. The bias elements 1106 may be compressed in a first region 1116 between the second coupler 1104 and the first coupler 1102 and extended in a second region 1118 between the second coupler and the first coupler, the second region on the opposite side of second coupler than the first region. The compression and extension together may deliver a force to the second coupler urging the center 1112 of the second coupler back to the center 1114 of the coupler assembly.

Figure 19:
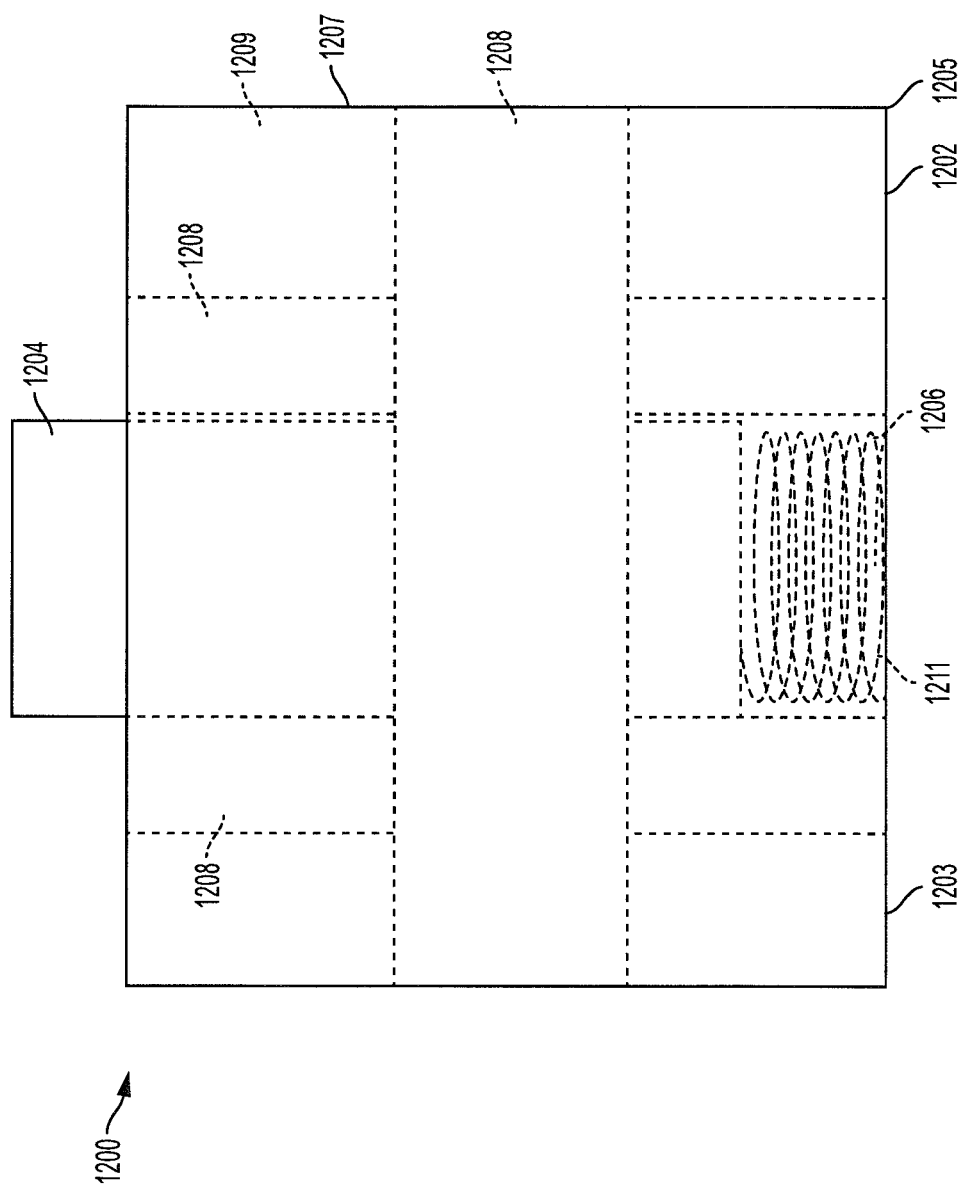
FIG. 19 is a schematic side view of another illustrative coupler assembly of the apparatus of FIG. 4.

FIG. 19 is schematic side view of another illustrative coupler assembly, generally indicated at 1200. Coupler assembly 1200 may include a first coupler 1202 attached to one of the first and second members of an inspection apparatus, a second coupler 1204 movably attached to the first coupler, and at least one bias element or elements 1206.

First coupler 1202 may be attached to the inspection apparatus by any appropriate means. The first coupler may be rigidly attached to the inspection apparatus, so that the first coupler and the inspection apparatus move through three dimensional space together. First coupler 1202 may form a casing or housing for one or more other components of the coupler assembly 1200. For example, first coupler 1202 may include a bottom wall 1203 having a perimeter 1205, and side wall(s) 1207 attached to, or formed with, the bottom wall. The bottom wall and the side wall(s) may define an open-topped container having an interior 1209. In some examples, the first coupler may include a top wall (not shown) configured to cover one or more other components of the coupler assembly.

Second coupler 1204 may be configured to be attached to a robotic arm, see FIGS. 4 and 11. Second coupler 1204 may be configured to move relative to the first coupler along at least two axes (or at least three axes). Second coupler 1204 may be a rod, a post, a shaft, or any other appropriate member and may have a nominal or equilibrium position within coupler assembly 1200.

Bias element or elements 1206 may be configured to urge the second coupler 1204 toward the nominal position. For example, bias elements 1206 may include a z-spring 1211 configured to allow for movement in the vertical direction as viewed in FIG. 19 while urging the second coupler toward the nominal position when the second coupler is displaced or moved from the nominal position.

Coupler assembly 1200 may include a set of plates 1208. The plates may be configured to partially hold the second coupler 1204 within the coupler assembly 1200. For example, the plates may be spaced to define an opening 1213 (see FIG. 20) sized to receive the second coupler. The plates may be configured to move within the interior of the first coupler. For example, the plates may be slidably received in the interior of the first coupler.

Figure 20:
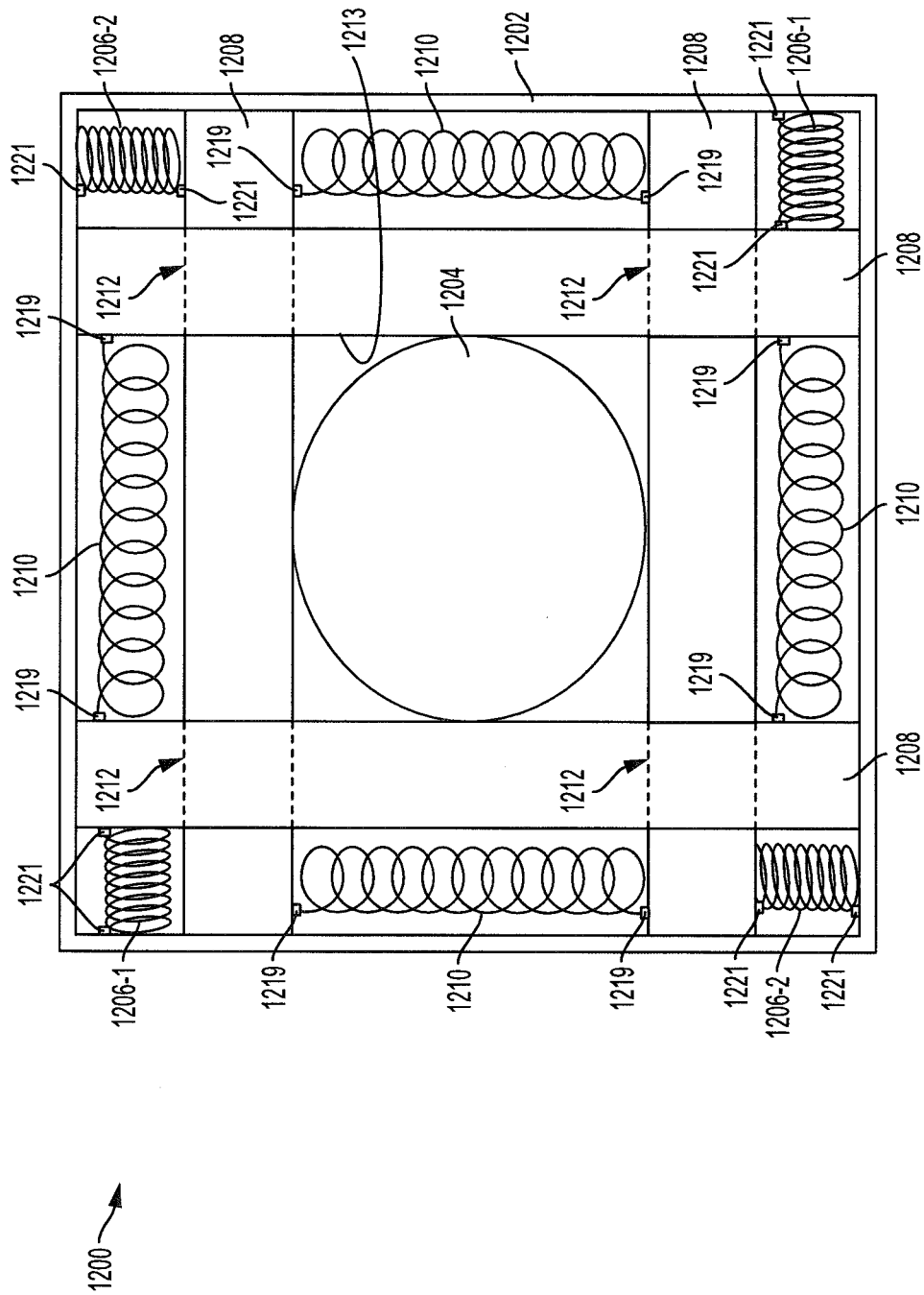
FIG. 20 is a schematic top view of the illustrative coupler assembly of FIG. 19.

FIG. 20 is a schematic top view of illustrative coupler assembly 1200. Coupler assembly 1200 may include one or more tension springs 1210. Tension springs 1210 may be configured to urge the plates 1208 toward one another and/or toward the second coupler, thereby gripping or otherwise holding the second coupler 1204.

Tension springs 1210 may be coupled to the plates by any appropriate means. For example, the end portion of the tension springs may be attached via plate connectors 1219, such as bolts, screws, rivets, etc. and/or the like. In some example, plate connectors 1108 may be openings, slots, or apertures sized to receive the first end portions of tension springs 1210. When coupler assembly 1200 includes tension spring(s) 1210, plates 1208 may be referred to as "spring-tensioned plates."

One or more of the plates 1208 may include through-passages 1212. The through-passages 1212 may allow the plates 1208 to pass or slide by and through one another. This may allow the spring-tensioned plates to extend between opposing sides of the first coupler 1202 in more than one horizontal direction, that is, in the plane of the view in FIG. 20.

Coupler assembly 1200 may include other bias elements 1206, such as one or more x-springs 1206-1 and/or y-springs 1206-2. These bias elements may be configured to urge the second coupler toward the nominal position when the second coupler is displaced or moved from the nominal position in either of the side-to-side directions as viewed in FIG. 20. The one or more x-springs and y-springs may apply one or more forces to the plates 1208 in order to urge the plates, and hence the second coupler, back to the nominal position.

X-springs 1206-1 and/or y-springs 1206-2 may be coupled to the plate and/or the first coupler by any appropriate means. For example, end portions of one or more of the x-springs and/or y-springs may be attached to plate(s) and/or the first coupler via spring connectors 1221, such as bolts, screws, rivets, etc. and/or the like. In some examples, spring connectors 1221 may be openings, slots, or apertures sized to receive end portions of the springs. In some examples, one or more end portions of the x-springs and/or y-springs may not be connected to the plates and/or the first coupler and may be supported in position via any suitable support structure(s). It will be appreciated than many orientations and dispositions of springs or other bias elements are possible to urge the second member to the nominal position, not just those orientations and dispositions shown in FIGS. 15-20.

Example 11

This section describes additional aspects and features of embodiments, presented without limitation as a series of paragraphs, some or all of which may be alphanumerically designated for clarity and efficiency. Each of these paragraphs can be combined with one or more other paragraphs, and/or with disclosure from elsewhere in this application in any suitable manner. Some of the paragraphs below expressly refer to and further limit other paragraphs, providing without limitation examples of some of the suitable combinations.

A0. An inspection apparatus for a composite end portion of a part having a contact surface and opposed first and second part surfaces, the tool comprising:
a first member having a first contact element;
a second member having a second contact element, the second member is movably connected to the first member, the first and second members are shaped to define a gap sized to receive the composite end portion such that the composite end portion is disposed between the first and second members when the composite end portion is received in the gap, wherein, when the composite end portion is received in the gap, the first contact element is configured to contact the first part surface and the second contact element is configured to contact the second part surface;
at least one ultrasonic array supported by at least one of the first and second members such that the at least one ultrasonic array is configured to transmit ultrasonic waves toward the composite end portion when the composite end portion is received in the gap; and
a fluid conduit through one of the first and second members, the conduit having first and second ends, the first end is configured to be coupled to a suction system, the second end is configured to be adjacent to the contact surface when the composite end portion is received in the gap.

A1. The apparatus of paragraph A0, further comprising a bias assembly configured to bias at least one of the first and second members toward the other of the at least one of the first and second members.

A2. The apparatus of any of paragraphs A0-A1, wherein the at least one ultrasonic array is configured to transmit ultrasonic waves toward the composite end portion and the first part surface when the composite end portion is received in the gap.

A3. The apparatus of any of paragraphs A0-A2, where the composite end portion includes a bevel surface, wherein the apparatus further comprises a filler element attached to one of the first and second members, the filler element includes first and second filler surfaces, wherein the first filler surface is complementary to the bevel surface and the second filler surface is co-planar with the first part surface when the composite end portion is received in the gap.

A4. The apparatus of paragraph A3, wherein, when the composite end portion is received in the gap, the first filler surface and the bevel surface form a first channel therebetween and the at least one ultrasonic array and the second filler surface form a second channel therebetween.

A5. The apparatus of paragraph A4, wherein the second channel includes first and second sides, and wherein, when the composite end portion is received in the gap, the first side is formed by the second filler surface and the first part surface and the second side is formed by the at least one ultrasonic array.

A6. The apparatus of any of paragraphs A4-A5, where the first channel includes first and second end portions and the second channel includes third and fourth end portions, further comprising a fluid inlet in one of the first and second members for receiving a fluid, and the fluid inlet is fluidly connected to the first and third end portions.

A7. The apparatus of paragraph A6, wherein the fluid inlet is configured to be coupled to a water source.

A8. The apparatus of paragraph A6, wherein the fluid inlet includes an aperture in the one of the first and second members, the aperture is configured, when the apparatus is submerged in liquid, to allow liquid to enter the first and second channels.

A9. The apparatus of any of paragraphs A6-A8, further comprising a fluid outlet in the one of the first and second members for discharging the fluid, the fluid outlet is fluidly connected to the second and fourth end portions.

A10. The apparatus of paragraph A9, wherein the fluid outlet is configured to be coupled to a drain system.

A11. The apparatus of any of paragraphs A3-A9, wherein the at least one ultrasonic array is configured to transmit ultrasonic waves toward the filler element and the first part surface when the composite end portion is received in the gap.

A12. The apparatus of any of paragraphs A0-A11, where the composite end portion includes a bevel surface and an end surface that is perpendicular to the first and second part surfaces, wherein the second end of the fluid conduit is configured to be adjacent to the end surface when the composite end portion is received in the gap.

A13. The apparatus of any of paragraphs A0-A12, where the composite end portion includes a bevel surface, further comprising a reflector plate supported by the other of the first and second members, the reflector plate is positioned to reflect ultrasonic waves transmitted by the at least one ultrasonic array through the bevel surface when the composite end portion is received in the gap and the apparatus and composite end portion are submerged in liquid.

A14. The apparatus of any of paragraphs A0-A13, wherein the at least one ultrasonic array includes first and second ultrasonic arrays, the first ultrasonic array is supported by the first member and the second ultrasonic array is supported by the second member.

A15. The apparatus of paragraph A14, wherein, when the composite end portion is received in the gap and the apparatus and composite end portion are submerged in liquid, the first ultrasonic array is configured to transmit ultrasonic waves toward the composite end portion and the second ultrasonic array is configured to detect ultrasonic waves.

A16. The apparatus of any of paragraphs A0-A15, further comprising a coupler assembly including a first coupler attached to one of the first and second members; a second coupler attached to the first coupler and configured to move relative to the first coupler along at least two axes, the second coupler is configured to be attached to a robotic arm; and at least one bias element configured to urge the second coupler toward a nominal position when the second coupler is moved away from the nominal position.

A17. The apparatus of paragraph A16, wherein the at least one bias element is a rubber ring configured to urge the second coupler toward the nominal position.

A18 The apparatus of paragraph A17, wherein the rubber ring includes a hole, and the second coupler is partially received in the hole.

A19. The apparatus of any of paragraphs A17-A18, wherein the first coupler includes an aperture, and the rubber ring is at least partially received in the aperture.

A20. The apparatus of paragraph A19, wherein the second coupler includes an end portion that is received in the hole, and the coupler assembly further includes a rubber pad attached to end portion A21. The apparatus of paragraph A16, wherein the at least one bias element is at least one spring configured to urge the second coupler toward the nominal position.

A22. The apparatus of paragraph A21, wherein the at least one spring includes first and second end portion, the first end portion is attached to the first coupler and the second end portion is attached to the second coupler.

A23. The apparatus of paragraph A16, wherein the first coupler includes a bottom wall having a perimeter and at least one sidewall attached to, or formed with, the bottom wall, the bottom wall and the at least one sidewall defining an open-topped container having an interior.

A24. The apparatus of paragraph A23, further comprising a plurality of plates slidably received in the interior and spaced to define an opening sized to receive the second coupler.

A25. The apparatus of paragraph A24, further comprising at least one spring configured to urge two or more plates of the plurality of plates toward the second coupler.

A26. The apparatus of any of paragraphs A24-A25, wherein the at least one bias element includes at least a first spring disposed between the second coupler and the bottom wall and configured to urge the second coupler toward the nominal position when the second coupler is moved toward or away from the bottom wall.

A27. The apparatus of any of paragraphs A24-A26, wherein the at least one bias element includes at least a second spring disposed between one or more plates of the plurality of plates and the at least one sidewall, the at least a second spring is configured to urge the second coupler toward the nominal position when the second coupler is moved relative to the first coupler and away from the nominal position.

A28. The apparatus of any of paragraphs A16-A27, wherein the second coupler is configured to move relative to the first coupler along at least two orthogonal axes.

B0. A method of inspecting a composite end portion of a part having a contact surface and opposed first and second part surfaces, the method comprising:
positioning an inspection apparatus such that the composite end portion is received in a gap of the inspection apparatus, a first contact element of the inspection apparatus contacts the first part surface, a second contact element of the inspection apparatus contacts the second part surface, and a second end of a fluid conduit of the inspection apparatus is adjacent to the contact surface;
activating a suction system fluidly connected to a first end of the fluid conduit to draw the contact surface toward the second end;
transmitting ultrasonic waves from at least one ultrasonic array of the inspection apparatus into the part;
detecting ultrasonic waves with the at least one ultrasonic array; and
moving the inspection apparatus along the composite end portion.

B1. The method of paragraph B0, where the composite end portion includes a bevel surface, and the apparatus includes a filler element having first and second filler surfaces, wherein the first filler surface is complementary to the bevel surface and the second filler surface is co-planar with the first part surface when the composite end portion is received in the gap, wherein transmitting ultrasonic waves includes transmitting ultrasonic waves from the at least one ultrasonic array through the filler element and into the part.

B2. The method of paragraph B1, wherein, when the composite end portion is received in the gap, the first filler surface and the bevel surface form a first channel therebetween and the at least one ultrasonic array and the second filler surface form a second channel therebetween, and wherein the method further comprises flowing fluid through the first and second channels.

B3. The method of any of paragraphs B0-B2, further comprising submerging the composite end portion and inspection apparatus in liquid.

B4. The method of paragraph B3, further comprising reflecting ultrasonic waves from the at least one ultrasonic array via at least one reflector plate of the inspection apparatus.

B5. The method of paragraph B3, wherein transmitting ultrasonic waves includes transmitting ultrasonic waves via a first ultrasonic array of the at least one ultrasonic array, and wherein detecting ultrasonic waves includes detecting ultrasonic waves via a second ultrasonic array of the at least one ultrasonic array.

B6. The method of any of paragraphs B0-B5, wherein moving the inspection apparatus along the composite end portion of the part includes moving the inspection apparatus via a robotic arm.

C0. A system for inspecting composite end portion of a part having a contact surface and opposed first and second part surfaces, comprising:
a robotic arm;
a controller assembly configured to control the robotic arm; and
an inspection apparatus coupled to the robotic arm, the inspection apparatus including:
a first member having a first contact element;
a second member having a second contact element, the second member is movably connected to the first member, the first and second members are shaped to define a gap sized to receive the composite end portion such that the composite end portion is disposed between the first and second members when the composite end portion is received in the gap, wherein, when the composite end portion is received in the gap, the first contact element is configured to contact the first part surface and the second contact element is configured to contact the second part surface;
at least one ultrasonic array supported by at least one of the first and second members such that the at least one ultrasonic array is configured to transmit ultrasonic waves toward the composite end portion when the composite end portion is received in the gap; and
a fluid conduit through one of the first and second members, the conduit having first and second ends, the first end is configured to be coupled to a suction system, the second end is configured to be adjacent to the contact surface when the composite end portion is received in the gap.

C1. The system of paragraph C0, wherein the controller assembly is configured to move the inspection apparatus along the composite end portion via the robotic arm.

C2. The system of any of paragraphs C0-C1, wherein the inspection apparatus further includes a coupler assembly including a first coupler attached to one of the first and second members; a second coupler attached to the first coupler and configured to move relative to the first coupler along at least two axes, the second coupler is coupled to the robotic arm; and at least one bias element configured to urge the second coupler toward a nominal position when the second coupler is moved away from the nominal position.

C3. The system of paragraph C2, wherein the at least one bias element is a rubber ring configured to urge the second coupler toward the nominal position.

C4 The system of paragraph C3, wherein the rubber ring includes a hole, and the second coupler is partially received in the hole.

C5. The system of any of paragraphs C3-C4, wherein the first coupler includes an aperture, and the rubber ring is at least partially received in the aperture.

C6. The system of paragraph C5, wherein the second coupler includes an end portion that is received in the hole, and the coupler assembly further includes a rubber pad attached to end portion C7. The system of paragraph C2, wherein the at least one bias element is at least one spring configured to urge the second coupler toward the nominal position.

C8. The system of paragraph C7, wherein the at least one spring includes first and second end portion, the first end portion is attached to the first coupler and the second end portion is attached to the second coupler.

C9. The system of paragraph C2, wherein the first coupler includes a bottom wall having a perimeter and at least one sidewall attached to, or formed with, the bottom wall, the bottom wall and the at least one sidewall defining an open-topped container having an interior.

C10. The system of paragraph C9, further comprising a plurality of plates slidably received in the interior and spaced to define an opening sized to receive the second coupler.

C11. The system of paragraph C10, further comprising at least one spring configured to urge two or more plates of the plurality of plates toward the second coupler.

C12. The system of any of paragraphs C10-C11, wherein the at least one bias element includes at least a first spring disposed between the second coupler and the bottom wall and configured to urge the second coupler toward the nominal position when the second coupler is moved toward or away from the bottom wall.

C13. The system of any of paragraphs C10-C12, wherein the at least one bias element includes at least a second spring disposed between one or more plates of the plurality of plates and the at least one sidewall, the at least a second spring is configured to urge the second coupler toward the nominal position when the second coupler is moved relative to the first coupler and away from the nominal position.

C14. The system of any of paragraphs C2-C13, wherein the second coupler is configured to move relative to the first coupler along at least two orthogonal axes.

D0. A reflector assembly for inspecting a composite end portion of a part having opposed first and second part surfaces, the composite end portion includes a bevel surface, the reflector assembly comprising:
a reflector plate having a base and an angled reflecting surface; and
a support assembly attached to the base and configured to support the reflector plate on the first part surface such that the base and the angled reflecting surface are adjacent to the first part surface and the bevel surface, respectively,
wherein the angled reflecting surface is configured to reflect ultrasonic waves transmitted from an ultrasonic array and through the bevel surface when (a) the support assembly supports the reflector plate on the first part surface, (b) the ultrasonic array is placed adjacent to the second part surface, (c) the reflector assembly, the composite end portion, and the ultrasonic array are submerged in liquid, and (d) the ultrasonic array transmits ultrasonic waves through the bevel surface.

D1. The reflector assembly of paragraph D0, where the composite end portion forms a first closed loop, wherein the angled reflecting surface forms a second closed loop that is adjacent to the first closed loop when the support assembly supports the reflector plate on the first part surface.

D2. The reflector assembly of any of paragraphs D0-D1, wherein the reflector plate further includes a parallel reflecting surface configured to reflect ultrasonic waves transmitted from the ultrasonic array and through the first part surface when (a) the support assembly supports the reflector plate on the first part surface, (b) the ultrasonic array is placed adjacent to the second part surface, (c) the reflector assembly, the composite end portion, and the ultrasonic array are submerged in liquid, and (d) the ultrasonic array transmits ultrasonic waves through the first part surface.

E0. A method of inspecting a composite end portion of a part having opposed first and second part surfaces, the composite end portion includes a bevel surface, the method comprising:
positioning an ultrasonic array adjacent to the second part surface;
positioning a reflector assembly on the first part surface adjacent to the composite end portion;
submerging the ultrasonic array, the reflector assembly, and the composite end portion in liquid;
transmitting ultrasonic waves from the ultrasonic array into the part;
reflecting ultrasonic waves transmitted from the ultrasonic array via the reflector assembly;
detecting ultrasonic waves with the ultrasonic array; and
moving the ultrasonic array along the composite end portion.

E1. The method of paragraph E0, wherein moving the ultrasonic array along the composite end portion includes moving the ultrasonic array along the composite end portion via a robotic arm.

Advantages, Features, Benefits

The different embodiments of the inspection apparatuses, systems, and methods described herein provide several advantages over known solutions for inspecting a composite end portion of a part. For example, the illustrative embodiments described herein allow a single apparatus to simultaneously inspect the trimmed end portion of a part and untrimmed portions of part proximate the trimmed end. Additionally, and among other benefits, illustrative embodiments described herein allow for self-aligning of the inspection apparatus. No known system or device can perform these functions. However, not all embodiments described herein provide the same advantages or the same degree of advantage.

CONCLUSION

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. To the extent that section headings are used within this disclosure, such headings are for organizational purposes only, and do not constitute a characterization of any claimed invention. The subject matter of the invention(s) includes all novel and nonobvious combinations and subcombinations of the various elements, features, functions, and/or properties disclosed herein. The following claims particularly point out certain combinations and subcombinations regarded as novel and nonobvious. Invention(s) embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the invention(s) of the present disclosure.

We claim:

1. An inspection apparatus for a composite end portion of a part having a contact surface and opposed first and second part surfaces, the apparatus comprising:
    a first member having a first contact element;
    a second member having a second contact element, the second member is movably connected to the first member, the first and second members are shaped to define a gap sized to receive the composite end portion such that the composite end portion is disposed between the first and second members when the composite end portion is received in the gap, wherein, when the composite end portion is received in the gap, the first contact element is configured to contact the first part surface and the second contact element is configured to contact the second part surface;
    at least one ultrasonic array supported by at least one of the first and second members such that the at least one ultrasonic array is configured to transmit ultrasonic waves toward the composite end portion when the composite end portion is received in the gap; and
    a fluid conduit through one of the first and second members, the conduit having first and second ends, the first end is configured to be coupled to a suction system, the second end is configured to be adjacent to the contact surface when the composite end portion is received in the gap.

2. The apparatus of claim 1, further comprising a bias assembly configured to bias at least one of the first and second members toward the other of the at least one of the first and second members.

3. The apparatus of claim 1, wherein the at least one ultrasonic array is configured to transmit ultrasonic waves toward the composite end portion and the first part surface when the composite end portion is received in the gap.

4. The apparatus of claim 1, where the composite end portion includes a bevel surface, wherein the apparatus further comprises a filler element attached to one of the first and second members, the filler element includes first and second filler surfaces, wherein the first filler surface is complementary to the bevel surface and the second filler surface is co-planar with the first part surface when the composite end portion is received in the gap.

5. The apparatus of claim 4, wherein, when the composite end portion is received in the gap, the first filler surface and the bevel surface form a first channel therebetween and the at least one ultrasonic array and the second filler surface form a second channel therebetween.

6. The apparatus of claim 5, wherein the second channel includes first and second sides, and wherein, when the composite end portion is received in the gap, the first side is formed by the second filler surface and the first part surface and the second side is formed by the at least one ultrasonic array.

7. The apparatus of claim 5, where the first channel includes first and second end portions and the second channel includes third and fourth end portions, further comprising a fluid inlet in one of the first and second members for receiving a fluid, and the fluid inlet is fluidly connected to the first and third end portions.

8. The apparatus of claim 7, wherein the fluid inlet is configured to be coupled to a water source.

9. The apparatus of claim 7, wherein the fluid inlet includes an aperture in the one of the first and second members, the aperture is configured, when the apparatus is submerged in liquid, to allow liquid to enter the first and second channels.

10. The apparatus of claim 7, further comprising a fluid outlet in the one of the first and second members for discharging the fluid, the fluid outlet is fluidly connected to the second and fourth end portions.

11. The apparatus of claim 10, wherein the fluid outlet is configured to be coupled to a drain system.

12. The apparatus of claim 4, wherein the at least one ultrasonic array is configured to transmit ultrasonic waves toward the filler element and the first part surface when the composite end portion is received in the gap.

13. The apparatus of claim 1, where the composite end portion includes a bevel surface and an end surface that is perpendicular to the first and second part surfaces, wherein the second end of the fluid conduit is configured to be adjacent to the end surface when the composite end portion is received in the gap.

14. The apparatus of claim 1, where the composite end portion includes a bevel surface, further comprising a reflector plate supported by the other of the first and second members, the reflector plate is positioned to reflect ultrasonic waves transmitted by the at least one ultrasonic array through the bevel surface when the composite end portion is received in the gap and the apparatus and composite end portion are submerged in liquid.

15. The apparatus of claim 1, wherein the at least one ultrasonic array includes first and second ultrasonic arrays, the first ultrasonic array is supported by the first member and the second ultrasonic array is supported by the second member.

16. The apparatus of claim 15, wherein, when the composite end portion is received in the gap and the apparatus and composite end portion are submerged in liquid, the first ultrasonic array is configured to transmit ultrasonic waves toward the composite end portion and the second ultrasonic array is configured to detect ultrasonic waves.

17. The apparatus of claim 1, further comprising a coupling assembly including:
    a first coupler attached to one of the first and second members;
    a second coupler attached to the first coupler and configured to move relative to the first coupler along at least two axes, the second coupler configured to be attached to a robotic arm; and
    at least one bias element configured to urge the second coupler toward a nominal position when the second coupler is moved away from the nominal position.

18. A method of inspecting a composite end portion of a part having a contact surface and opposed first and second part surfaces, the method comprising:
    positioning an inspection apparatus such that the composite end portion is received in a gap of the inspection apparatus, a first contact element of the inspection apparatus contacts the first part surface, a second contact element of the inspection apparatus contacts the second part surface, and a second end of a fluid conduit of the inspection apparatus is adjacent to the contact surface;
    activating a suction system fluidly connected to a first end of the fluid conduit to draw the contact surface toward the second end;

transmitting ultrasonic waves from at least one ultrasonic array of the inspection apparatus into the part;
detecting ultrasonic waves with the at least one ultrasonic array; and
moving the inspection apparatus along the composite end portion.

19. The method of claim 18, where the composite end portion includes a bevel surface, and the apparatus includes a filler element having first and second filler surfaces, wherein the first filler surface is complementary to the bevel surface and the second filler surface is co-planar with the first part surface when the composite end portion is received in the gap, wherein transmitting ultrasonic waves includes transmitting ultrasonic waves from the at least one ultrasonic array through the filler element and into the part.

20. The method of claim 19, wherein, when the composite end portion is received in the gap, the first filler surface and the bevel surface form a first channel therebetween and the at least one ultrasonic array and the second filler surface form a second channel therebetween, and wherein the method further comprises flowing fluid through the first and second channels.

21. The method of claim 18, further comprising submerging the composite end portion and inspection apparatus in liquid.

22. The method of claim 21, further comprising reflecting ultrasonic waves from the at least one ultrasonic array via at least one reflector plate of the inspection apparatus.

23. The method of claim 21, wherein transmitting ultrasonic waves includes transmitting ultrasonic waves via a first ultrasonic array of the at least one ultrasonic array, and wherein detecting ultrasonic waves includes detecting ultrasonic waves via a second ultrasonic array of the at least one ultrasonic array.

24. The method of claim 18, wherein moving the inspection apparatus along the composite end portion of the part includes moving the inspection apparatus via a robotic arm.

25. A system for inspecting composite end portion of a part having a contact surface and opposed first and second part surfaces, comprising:
a robotic arm;
a controller assembly configured to control the robotic arm; and
an inspection apparatus coupled to the robotic arm, the inspection apparatus including:
a first member having a first contact element;
a second member having a second contact element, the second member is movably connected to the first member, the first and second members are shaped to define a gap sized to receive the composite end portion such that the composite end portion is disposed between the first and second members when the composite end portion is received in the gap, wherein, when the composite end portion is received in the gap, the first contact element is configured to contact the first part surface and the second contact element is configured to contact the second part surface;
at least one ultrasonic array supported by at least one of the first and second members such that the at least one ultrasonic array is configured to transmit ultrasonic waves toward the composite end portion when the composite end portion is received in the gap; and
a fluid conduit through one of the first and second members, the conduit having first and second ends, the first end is configured to be coupled to a suction system, the second end is configured to be adjacent to the contact surface when the composite end portion is received in the gap.

26. The system of claim 25, wherein the controller assembly is configured to move the inspection apparatus along the composite end portion via the robotic arm.

27. The system of claim 25, wherein the inspection apparatus includes a coupler assembly having:
a first coupler attached to one of the first and second members;
a second coupler attached to the first coupler and configured to move relative to the first coupler along at least two axes, the second coupler is coupled to the robotic arm; and
at least one bias element configured to urge the second coupler toward a nominal position when the second coupler is moved away from the nominal position.

28. A reflector assembly for inspecting a composite end portion of a part having opposed first and second part surfaces, the composite end portion includes a bevel surface, the reflector assembly comprising:
a reflector plate having a base and an angled reflecting surface; and
a support assembly attached to the base and configured to support the reflector plate on the first part surface such that the base and the angled reflecting surface are adjacent to the first part surface and the bevel surface, respectively,
wherein the angled reflecting surface is configured to reflect ultrasonic waves transmitted from an ultrasonic array and through the bevel surface when (a) the support assembly supports the reflector plate on the first part surface, (b) the ultrasonic array is placed adjacent to the second part surface, (c) the reflector assembly, the composite end portion, and the ultrasonic array are submerged in liquid, and (d) the ultrasonic array transmits ultrasonic waves through the bevel surface.

29. The reflector assembly of claim 28, where the composite end portion forms a first closed loop, wherein the angled reflecting surface forms a second closed loop that is adjacent to the first closed loop when the support assembly supports the reflector plate on the first part surface.

30. The reflector assembly of claim 28, wherein the reflector plate further includes a parallel reflecting surface configured to reflect ultrasonic waves transmitted from the ultrasonic array and through the first part surface when (a) the support assembly supports the reflector plate on the first part surface, (b) the ultrasonic array is placed adjacent to the second part surface, (c) the reflector assembly, the composite end portion, and the ultrasonic array are submerged in liquid, and (d) the ultrasonic array transmits ultrasonic waves through the first part surface.

31. A method of inspecting a composite end portion of a part having opposed first and second part surfaces, the composite end portion includes a bevel surface, the method comprising:
positioning an ultrasonic array adjacent to the second part surface;
positioning a reflector assembly on the first part surface adjacent to the composite end portion;
submerging the ultrasonic array, the reflector assembly, and the composite end portion in liquid;
transmitting ultrasonic waves from the ultrasonic array into the part;
reflecting ultrasonic waves transmitted from the ultrasonic array via the reflector assembly;
detecting ultrasonic waves with the ultrasonic array; and moving the ultrasonic array along the composite end portion.

32. The method of claim 31, wherein moving the ultrasonic array along the composite end portion includes moving the ultrasonic array along the composite end portion via a robotic arm.

\* \* \* \* \*